(12) United States Patent
Mostafavi

(10) Patent No.: US 8,571,639 B2
(45) Date of Patent: *Oct. 29, 2013

(54) SYSTEMS AND METHODS FOR GATING MEDICAL PROCEDURES

(75) Inventor: Hassan Mostafavi, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 619 days.

This patent is subject to a terminal disclaimer.

(21) Appl. No.: 10/655,920

(22) Filed: Sep. 5, 2003

(65) Prior Publication Data
US 2005/0054916 A1 Mar. 10, 2005

(51) Int. Cl.
A61B 5/00 (2006.01)

(52) U.S. Cl.
USPC ........... 600/428; 600/425; 600/407; 600/413; 378/65

(58) Field of Classification Search
USPC .................... 600/413, 428; 378/65
See application file for complete search history.

(56) References Cited

U.S. PATENT DOCUMENTS

| | | | |
|---|---|---|---|
| 3,861,807 A | 1/1975 | Lescrenier | |
| 3,871,360 A | 3/1975 | Van Horn et al. | |
| 3,952,201 A | 4/1976 | Hounsfield | |
| 3,974,386 A | 8/1976 | Mistretta et al. | |
| 4,031,884 A | 6/1977 | Henzel | |
| 4,262,306 A | 4/1981 | Renner | |
| 4,289,142 A | 9/1981 | Kearns | |
| 4,335,427 A | 6/1982 | Hunt et al. | |
| 4,387,722 A | 6/1983 | Kearns | |
| 4,463,425 A | 7/1984 | Hirano et al. | |
| 4,545,384 A | 10/1985 | Kawachi | |
| 4,663,591 A | 5/1987 | Pelc et al. | |
| 4,672,651 A * | 6/1987 | Horiba et al. | 378/62 |
| 4,686,999 A | 8/1987 | Snyder et al. | |
| 4,710,717 A | 12/1987 | Pelc et al. | |
| 4,727,882 A | 3/1988 | Schneider et al. | |
| 4,802,486 A | 2/1989 | Goodman et al. | |

(Continued)

FOREIGN PATENT DOCUMENTS

| | | |
|---|---|---|
| DE | 43 41 324 A1 | 6/1995 |
| DE | 19856467 | 5/2000 |

(Continued)

OTHER PUBLICATIONS

International Search Report, dated Jan. 30, 2006 for PCT/US2004/028571).

(Continued)

Primary Examiner — Unsu Jung
Assistant Examiner — Amanda Lauritzen
(74) Attorney, Agent, or Firm — Vista IP Law Group, LLP

(57) ABSTRACT

A method of performing physiological gating in a medical procedure includes acquiring a sequence of images having at least a first image and a second image of a target region, determining a first composite image based on the first and second images, and gating a medical procedure based on the composite image. A method of performing a medical procedure includes providing a plurality of templates, each of the templates having an image and treatment data, acquiring an input image, registering the input image with one of the templates, and performing a medical procedure based on the treatment data of the one of the templates that is registered with the input image.

53 Claims, 11 Drawing Sheets

(56) References Cited

U.S. PATENT DOCUMENTS

| | | | |
|---|---|---|---|
| 4,853,771 A | 8/1989 | Witriol et al. | |
| 4,895,160 A | 1/1990 | Reents | |
| 4,928,692 A | 5/1990 | Goodman et al. | |
| 4,971,065 A | 11/1990 | Pearce | |
| 4,994,965 A | 2/1991 | Crawford et al. | |
| 5,051,903 A | 9/1991 | Pelc et al. | |
| 5,080,100 A | 1/1992 | Trotel | |
| 5,107,845 A | 4/1992 | Guern et al. | |
| 5,109,435 A | 4/1992 | Lo et al. | |
| 5,134,472 A | 7/1992 | Abe | |
| 5,150,426 A | 9/1992 | Bahn et al. | |
| 5,199,424 A | 4/1993 | Sullivan et al. | |
| 5,207,223 A | 5/1993 | Adler et al. | |
| 5,262,945 A | 11/1993 | DeCarli et al. | |
| 5,265,142 A | 11/1993 | Hsieh | |
| 5,271,055 A | 12/1993 | Hsieh et al. | |
| 5,279,309 A | 1/1994 | Taylor et al. | |
| 5,285,786 A | 2/1994 | Fujii | |
| 5,295,483 A | 3/1994 | Nowacki et al. | |
| 5,315,630 A | 5/1994 | Sturm et al. | |
| 5,363,844 A | 11/1994 | Riederer et al. | |
| 5,377,681 A | 1/1995 | Drane | |
| 5,389,101 A | 2/1995 | Heilbrun et al. | |
| 5,394,875 A | 3/1995 | Lewis et al. | |
| 5,396,875 A | 3/1995 | Kotwicki et al. | |
| 5,446,548 A | 8/1995 | Gerig et al. | |
| 5,448,548 A | 9/1995 | Taneya et al. | |
| 5,482,042 A | 1/1996 | Fujita | |
| 5,513,646 A | 5/1996 | Lehrman et al. | |
| 5,515,849 A | 5/1996 | Murashita et al. | |
| 5,522,382 A | 6/1996 | Sullivan et al. | |
| 5,531,520 A | 7/1996 | Grimson et al. | |
| 5,535,289 A | 7/1996 | Ito | |
| 5,538,494 A | 7/1996 | Matsuda | |
| 5,565,777 A | 10/1996 | Kanayama et al. | |
| 5,573,012 A | 11/1996 | McEwan | |
| 5,582,182 A | 12/1996 | Hillsman | |
| 5,588,430 A | 12/1996 | Bova et al. | |
| 5,603,318 A | 2/1997 | Heilbrun et al. | |
| 5,619,995 A | 4/1997 | Lobodzinski | |
| 5,622,187 A | 4/1997 | Carol | |
| 5,638,819 A | 6/1997 | Manwaring et al. | |
| 5,662,111 A | 9/1997 | Cosman | |
| 5,662,112 A | 9/1997 | Heid | |
| 5,727,554 A | 3/1998 | Kalend et al. | |
| 5,738,102 A | 4/1998 | Lemelson | |
| 5,764,723 A | 6/1998 | Weinberger et al. | |
| 5,771,310 A | 6/1998 | Vannah | |
| 5,784,431 A * | 7/1998 | Kalend et al. | 378/65 |
| 5,794,621 A | 8/1998 | Hogan et al. | |
| 5,820,553 A | 10/1998 | Hughes | |
| 5,823,192 A | 10/1998 | Kalend et al. | |
| 5,828,770 A | 10/1998 | Leis et al. | |
| 5,836,954 A | 11/1998 | Heilbrun et al. | |
| 5,891,034 A | 4/1999 | Bucholz | |
| 5,906,202 A | 5/1999 | Schuster et al. | |
| 5,912,656 A | 6/1999 | Tham et al. | |
| 5,924,989 A | 7/1999 | Polz | |
| 5,954,647 A | 9/1999 | Bova et al. | |
| 5,982,915 A | 11/1999 | Doi et al. | |
| 5,993,390 A * | 11/1999 | Savord et al. | 600/437 |
| 5,993,397 A | 11/1999 | Branson | |
| 5,997,883 A | 12/1999 | Epstein et al. | |
| 6,061,644 A | 5/2000 | Leis | |
| 6,067,373 A | 5/2000 | Ishida et al. | |
| 6,075,557 A | 6/2000 | Holliman et al. | |
| 6,076,005 A | 6/2000 | Sontag et al. | |
| 6,084,939 A | 7/2000 | Tamura | |
| 6,125,166 A * | 9/2000 | Takeo | 378/98.12 |
| 6,138,302 A | 10/2000 | Sashin et al. | |
| 6,144,874 A | 11/2000 | Du | |
| 6,144,875 A | 11/2000 | Schweikard et al. | |
| 6,146,390 A | 11/2000 | Heilbrun et al. | |
| 6,165,181 A | 12/2000 | Heilbrun et al. | |
| 6,185,445 B1 | 2/2001 | Knuttel | |
| 6,185,446 B1 | 2/2001 | Carlsen, Jr. | |
| 6,198,959 B1 | 3/2001 | Wang | |
| 6,216,029 B1 | 4/2001 | Paltieli | |
| 6,259,943 B1 | 7/2001 | Cosman et al. | |
| 6,266,443 B1 | 7/2001 | Vetro et al. | |
| 6,269,140 B1 | 7/2001 | Takagi et al. | |
| 6,272,368 B1 | 8/2001 | Alexandrescu | |
| 6,296,613 B1 | 10/2001 | Emmenegger et al. | |
| 6,300,974 B1 | 10/2001 | Viala et al. | |
| 6,307,914 B1 | 10/2001 | Kunieda et al. | |
| 6,333,991 B1 | 12/2001 | Schreiber et al. | |
| 6,348,058 B1 | 2/2002 | Melkent et al. | |
| 6,370,217 B1 | 4/2002 | Hu et al. | |
| 6,370,417 B1 | 4/2002 | Horbaschek et al. | |
| 6,375,612 B1 | 4/2002 | Guichon et al. | |
| 6,398,739 B1 | 6/2002 | Sullivan et al. | |
| 6,405,072 B1 | 6/2002 | Cosman | |
| 6,434,215 B1 | 8/2002 | Cesmeli | |
| 6,434,507 B1 | 8/2002 | Clayton et al. | |
| 6,473,634 B1 | 10/2002 | Barni | |
| 6,473,635 B1 | 10/2002 | Rasche | |
| 6,475,156 B1 | 11/2002 | Vega | |
| 6,486,604 B1 | 11/2002 | Bradatsch | |
| 6,487,274 B2 | 11/2002 | Bertsche | |
| 6,501,981 B1 | 12/2002 | Schweikard et al. | |
| 6,526,117 B1 | 2/2003 | Okerlund et al. | |
| 6,526,156 B1 * | 2/2003 | Black et al. | 382/103 |
| 6,527,443 B1 | 3/2003 | Vilsmeier et al. | |
| 6,535,574 B1 | 3/2003 | Collins et al. | |
| 6,546,124 B1 | 4/2003 | Hopple et al. | |
| 6,569,092 B1 | 5/2003 | Guichon et al. | |
| 6,611,617 B1 | 8/2003 | Crampton | |
| 6,621,889 B1 | 9/2003 | Mostafavi | |
| 6,635,021 B1 | 10/2003 | Sullivan et al. | |
| 6,661,617 B1 | 12/2003 | Hipwell, Jr. et al. | |
| 6,665,370 B2 | 12/2003 | Bruder et al. | |
| 6,678,399 B2 | 1/2004 | Doi et al. | |
| 6,690,965 B1 * | 2/2004 | Riaziat et al. | 600/428 |
| 6,697,761 B2 | 2/2004 | Akatsuka et al. | |
| 6,705,315 B2 | 3/2004 | Sullivan et al. | |
| 6,724,930 B1 | 4/2004 | Kosaka et al. | |
| 6,731,970 B2 | 5/2004 | Schlossbauer et al. | |
| 6,766,064 B1 | 7/2004 | Langan et al. | |
| 6,888,919 B2 | 5/2005 | Graf | |
| 6,904,126 B2 | 6/2005 | Endo | |
| 6,937,696 B1 | 8/2005 | Mostafavi | |
| 6,940,945 B2 | 9/2005 | Maschke | |
| 6,980,679 B2 | 12/2005 | Jeung et al. | |
| 6,984,208 B2 | 1/2006 | Zheng | |
| 7,003,146 B2 | 2/2006 | Eck et al. | |
| 7,006,862 B2 * | 2/2006 | Kaufman et al. | 600/523 |
| 7,058,204 B2 | 6/2006 | Hildreth et al. | |
| 7,062,078 B2 * | 6/2006 | Weese et al. | 382/131 |
| 7,103,400 B2 * | 9/2006 | Ossmann et al. | 600/428 |
| 7,123,758 B2 | 10/2006 | Jeung et al. | |
| 7,158,610 B2 | 1/2007 | Mostafavi | |
| 7,221,733 B1 * | 5/2007 | Takai et al. | 378/65 |
| 7,227,925 B1 * | 6/2007 | Mansfield et al. | 378/65 |
| 7,257,436 B2 | 8/2007 | Sasaki et al. | |
| 7,260,426 B2 * | 8/2007 | Schweikard et al. | 600/407 |
| 7,306,564 B2 | 12/2007 | Nakatani et al. | |
| 7,314,451 B2 | 1/2008 | Halperin et al. | |
| 7,349,522 B2 * | 3/2008 | Yan et al. | 378/65 |
| 7,403,638 B2 | 7/2008 | Jeung et al. | |
| 7,415,169 B2 * | 8/2008 | Florent et al. | 382/294 |
| 7,609,810 B2 * | 10/2009 | Yi et al. | 378/65 |
| 7,769,430 B2 | 8/2010 | Mostafavi | |
| 2002/0023652 A1 | 2/2002 | Riaziat et al. | |
| 2002/0091314 A1 | 7/2002 | Schlossbauer et al. | |
| 2002/0097155 A1 | 7/2002 | Cassel et al. | |
| 2002/0115931 A1 | 8/2002 | Strauss et al. | |
| 2002/0118274 A1 | 8/2002 | Yahashi | |
| 2002/0188194 A1 | 12/2002 | Cosman | |
| 2003/0007593 A1 | 1/2003 | Heuscher et al. | |
| 2003/0007601 A1 | 1/2003 | Jaffray et al. | |
| 2003/0026758 A1 * | 2/2003 | Baker | 424/9.1 |
| 2003/0063292 A1 | 4/2003 | Mostafavi | |
| 2003/0072419 A1 | 4/2003 | Bruder et al. | |
| 2003/0086596 A1 | 5/2003 | Hipp et al. | |

(56) References Cited

U.S. PATENT DOCUMENTS

| | | | |
|---|---|---|---|
| 2003/0099388 A1 | 5/2003 | Doi et al. | |
| 2003/0135103 A1 | 7/2003 | Mistretta | |
| 2003/0188757 A1 | 10/2003 | Yanof et al. | |
| 2003/0210812 A1 | 11/2003 | Khamene et al. | |
| 2004/0005088 A1 | 1/2004 | Jeung et al. | |
| 2004/0068169 A1 | 4/2004 | Mansfield et al. | |
| 2004/0071337 A1 | 4/2004 | Jeung et al. | |
| 2004/0082853 A1 | 4/2004 | Sasaki et al. | |
| 2004/0092815 A1 | 5/2004 | Schweikard et al. | |
| 2004/0092816 A1* | 5/2004 | Ossmann et al. | 600/428 |
| 2004/0097805 A1* | 5/2004 | Verard et al. | 600/428 |
| 2004/0114718 A1 | 6/2004 | Brown | |
| 2004/0116804 A1 | 6/2004 | Mostafavi | |
| 2004/0215077 A1* | 10/2004 | Witt et al. | 600/443 |
| 2004/0218719 A1 | 11/2004 | Brown et al. | |
| 2004/0234115 A1 | 11/2004 | Zijp et al. | |
| 2004/0254773 A1 | 12/2004 | Zhang et al. | |
| 2005/0002546 A1 | 1/2005 | Florent et al. | |
| 2005/0027196 A1* | 2/2005 | Fitzgerald | 600/436 |
| 2005/0053267 A1* | 3/2005 | Mostafavi | 382/128 |
| 2005/0054916 A1 | 3/2005 | Mostafavi | |
| 2005/0080336 A1* | 4/2005 | Byrd et al. | 600/428 |
| 2005/0113672 A1* | 5/2005 | Salla et al. | 600/413 |
| 2005/0113711 A1 | 5/2005 | Nakatani et al. | |
| 2005/0201510 A1 | 9/2005 | Mostafavi | |
| 2005/0283068 A1 | 12/2005 | Zuccolotto et al. | |
| 2006/0165267 A1* | 7/2006 | Wyman et al. | 382/128 |
| 2006/0241443 A1* | 10/2006 | Whitmore et al. | 600/439 |
| 2007/0053491 A1* | 3/2007 | Schildkraut et al. | 378/65 |
| 2007/0053494 A1* | 3/2007 | Mostafavi | 378/98.12 |
| 2007/0189455 A1* | 8/2007 | Allison | 378/95 |
| 2008/0144772 A1* | 6/2008 | Yi et al. | 378/65 |

FOREIGN PATENT DOCUMENTS

| | | |
|---|---|---|
| EP | 0866607 A2 | 9/1998 |
| EP | 1 050 272 A | 11/2000 |
| FI | 79458 | 9/1989 |
| JP | 58-136334 | 8/1983 |
| JP | 61-220628 | 9/1986 |
| JP | 4-364677 | 12/1992 |
| JP | 6-292085 | 10/1994 |
| JP | 7-275237 | 10/1995 |
| JP | 10-289321 | 10/1998 |
| JP | 2000-262511 | 9/2000 |
| JP | 2000-325339 | 11/2000 |
| JP | 2002-090118 | 3/2002 |
| JP | 2002-533889 | 10/2002 |
| WO | WO 98/16151 | 4/1998 |
| WO | WO 98/30977 | 7/1998 |
| WO | WO 98/38908 | 9/1998 |
| WO | WO 98/52635 | 11/1998 |
| WO | 00/24466 | 5/2000 |
| WO | WO 00/24333 | 5/2000 |
| WO | 02/26125 A2 | 4/2002 |
| WO | 00/77818 A1 | 10/2002 |
| WO | WO 02/085455 | 10/2002 |
| WO | WO 03/003796 | 1/2003 |

OTHER PUBLICATIONS

Adams, W.B. et al. "Correlator Compensation Requirements for Passive Time-Delay Estimation with Moving Source or Receivers" IEEE (Apr. 1980) ASSP-28(2):158-168.

Ahlstrom, K.H. et al. "Pulmonary MR Angiography with Ultrasmall Superparamagnitic Iron Oxide Particles as a Blood Pool Agent and a Navigtor Echo for Respiratory Gating: Pilot Study" Radiology (Jun. 1999) 211(3):865-869.

Axel, L. et al. "Respiratory Effects in Two-Dimensional Fourier Transform MR Imaging" Radiology (Sep. 1986) 160(3):795-801.

Balter, J.M. et al.; "Uncertainties in CT-Based Radiation Therapy Treatment Planning Associated With Patient Breathing"; Int. J. Radial. Oncol.. Bioi., Phys. 36; pp. 167-174 (Aug. 1996).

Bankman, I.N. et al. "Optimal Detection, Classification, and Superposition Resolution in Neural Waveform Recordings" IEEE ) Aug. 1993) 40(8):836-841).

Baroni, G. and G. Ferrigno "Real-time Motion Analysis for Definition and Control of Patient Position in Radiotherapy" SPIE 0-81942084-0/96 2709:506-515.

Bellenger, N.G. et al.; "Left Ventricular Quantification in Heart Failure by Cardiovascular MR Using Prospective OS Respiratory Navigator Gating: Comparison With Breath-Hold Acquisition"; J. Magn. Reson. Imaging 11; pp. 411-417; (Apr. 2000).

Cho, K. et al.; "Development of Respiratory Gated Myocardial SPECT System", J. Nucl. Cardial. 6; pp. 20-28; (Jan. 1-Feb. 1999).

Danias, P.G. et al. "Prospective Navigator Correction of Image Position for Coronary MR Angiography" Radiology (Jun. 1997) 203:733-736.

Davies, S.C. et al.; "Ultrasound Quantitation of Respiratory Organ Motion in The Upper Abdomen"; Br. J. Radiol. 67; pp. 1096-1102 (Nov. 1994).

Du, Y.P. "Prospective navigator gating with a dual acceptance window technique to reduce respiratory motion artifacts in 3D MR coronary angiography" Int'l J. Cardiovascular Imaging (2003) 19:157-162.

Du, Y.P. et al. "A comparison of prospective and retrospective respiratory navigator gating in 3D MR coronary angiography" Int'l J. Cardiovascular Imaging (2001) 17:287-294.

Ehman, R.L. et al.; "Magnetic Resonance Imaging With Respiratory Gating: Techniques and Advantages"; Am. J. Roenlgenoll43; pp. 1175-1182 (Dec. 1984).

Fee, M.S. et al. "Automatic Sorting of Mulitple Unit Neuronal Signals in the Presence of Anisotropic and non-Gaussian Variability" J. Neuroscience Methods (1996) 69:175-188.

Felblinger, J. et al. "Effects of physiologic motion of the human brain upon quantitative H-MRS: analysis and correction by retrogating" NMR in Biomedicine (1998) 11:107-114.

Fishbein, K.W. et al. "The lever-coil: A simple, inexpensive sensor for respiratory and cardiac motion in MRI experiments" Magnetic Resonance Imaging (2001) 19:881-889.

Frolich, H.et al.;"A Simple Device for Breath-Level Monitoring During CT"; Radiology 156; p. 235 (Jul. 1985).

Gerig, L.H. et al. "The Development and Clinical Application of a Patient Position Monitoring System" Ottawa Regional Cancer Centre, General Division, 501 Smyth Rd., Ottawa, Ontario, Canada K1H8L6; National Research Council, IIT, Ottawa, Ontario, Canada K1A OR6; SpIE Videometrics III (1994) 2350:59-72.

Haacke, E.M. and G.W. Lenz "Improving MR Image Quality in the Presence of Motion by Using Rephasing Gradients" AJR (Jun. 1987) 148:1251-1258.

Hanley, J. et al.; "Deep Inspiration Breath-Hold Technique for Lung Tumors: the Potential Value of Target CS Immobilization and Reduced Lung Density in Dose Escalation"; Int. J. Radial. Oncol., Biol. Phys. 45; pp. 603-611 (Oct. 1999).

Henkelman, R.M. et al.; "How Important is Breathing in Radiation Therapy of the Thorax?"; Int. J. Radiat. Onco/., Bioi., Phys. 8; pp. 2005-2010 (Nov. 1982).

Hofman, M.B.M. et al.; "MRI of Coronary Arteries: 20 Breath-Hold vs. 3D Respiratory-Gated Acquisition"; J. of Compo Assisted Tomography 19; pp. 56-62 (Jan. 1-Feb. 1995).

Huber, A. et al. "Navigator Echo-Based Respiratory Gating for Three-Dimensional MR Coronary Angiography: Results from Healthy Volunteers and Patients with Proximal Coronary Artery Stenoses" AJR (Jul. 1999) 173:95-101.

Iwasawa, Tae, et al.; "Normal In-Plane Respiratory Motion of the Bilateral Hemidiaphragms Evaluated by Sequentially Subtracted Fast Magnetic Resonance Images"; Journal of Thoracic Imaging; 1999; vol. 14, No. 2; pp. 130-134.

Johnson, L.S. et al.; "Initial Clinical Experience With a Video-Based Patient Positioning System"; Int. J. Radial. Oncol. Biol. Phys. 45; pp. 205-213; (Aug. 1999).

Jolesz, Ferenc M.D., et al.; "Image-Guided Procedures and the Operating Room of the Future"; Radiology; SPL Technical Report #48; May 1997: 204:601-612.

(56) References Cited

OTHER PUBLICATIONS

Josefsson, T. et al. "A Flexible High-Precision Video System for Digital Recording of Motor Acts Through Lightweight Reflex Markers" Computer Methods & Programs in Biomedicine (1996) 49:119-129.

Kachelriess, Marc, et al.; "Electrocardiogram-correlated Image Reconstruction From Subsecond Spiral Computed Tomography Scans of the Heart"; Med. Phys. 25(12); Dec. 1998; pp. 2417-2431.

Keatley, E. et al.; "Computer Automated Diaphragm Motion Quantification in a Fluoroscopic Movie"; Dept. of Medical Physics, Memorial Sloan-Kettering Cancer Center, New York; 3 pp. 1749-1751.

Kim, W.S., et al.; "Extension of Cardiac and Respiratory Motion Cycles by Use of Projection Data and Its Applications to NMR Imaging"; Magnetic Resonance in Medicine 13; 1990; pp. 25-37.

Korin, H.W. et al.; "Respiratory Kinematics of the Upper Abdominal Organs: A Quantitative Study"; Magn. Rason. Med. 23; pp. 172-178 (Jan. 1992).

Kubo, H.D. et al.; "Breathing-Synchronized Radiotherapy Program at the University of California Davis Cancer Center"; Med. Phys. 27(2); Feb. 2000; pp. 346-353.

Kubo, H.D. et al.; "Compatibility of Varian 2100C Gated Operations With Enhanced Dynamic Wedge and IMRT Dose Delivery"; Med. Phys. 27; pp. 1732-1738; (Aug. 2000).

Kubo, H.D. et al.; "Potential and Role of a Prototype Amorphous Silicon Array Electronic Portal Imaging Device in Breathing Synchronized Radiotherapy"; Med. Phys. 26(11); Nov. 1999; pp. 2410-2414.

Kubo, H.D. et al.; "Respiration Gated Radiotherapy Treatment: A Technical Study"; Phys. Mad. Bioi. 41; pp. 83-91;(1996).

Kutcher, G.J. et al.; "Control; Correction, and Modeling of Setup Errors and Organ Motion", Semin. Radiat. Oncol. 5; pp. 134-145 (Apr. 1995).

Lee, M.W. and I. Cohen "Human Body Tracking with Auxiliary Measurements" IEEE International Workshop on Analysis and Modeling of Faces and Gestures (2003) 8 pages, located at htt/:///iris.usc.edu/~icohen/projects/human/body/index.htm.

Lethimonnier, F. et al.; "Three-Dimensional. Coronary Artery MR Imaging Using Prospective Real-Time Respiratory DE Navigator and Linear Phase Shift Processing: Comparison With Conventional Coronary Angiography", Magn. Reson. Imaaine 17; DO. 1111-1120; (1999).

Lewis, C.E. et al.; "Comparison of Respiratory Triggering and Gating Techniques for the Removal of Respiratory Artifacts in MR Imaging"; Radiology 160; pp. 803-810; (Sep. 1986).

Li, D. et al.; "Coronary Arteries: Three-dimensional MR Imaging With Retrospective Respiratory Gating"; Radiology; Dec. 1996; vol. 201; No. 3.; pp. 857-863.

Lieberman, J.M. et al. Gated Magnetic Resonance Imaging of the Normal Diseased Heart: Radiology (Aug. 1984) 152:465-470.

Lopresti, B.J. et al. "Implementation and Performance of an Optical Motion Tracking System for High Resolution Brain PET Imaging" IEEE Transactions on Nuclear Science (Dec. 1999) 46(6):2059-2067.

Luker, Gary D., et al.; "Ghosting of Pulmonary Nodules With Respiratory Motion: Comparison of Helical and ConvenHonal CT Using an In Vitro Pediatric Model"; AJR:167; Nov. 1996; pp. 1189-1193.

Mageras, G. et al.; "Initial Clinical Evaluation of a Respiratory Gating Radiotherapy System"; 22nd Annual EMBS International Conference, Chicago. IL.; pp. 2124-2127; (Jul. 23-28, 2000).

Mageras, G.S. et al.; "Respiratory Motion-Induced Treatment Uncertainties"; Patras Medical Physics 99- VI International Conference on Medical Physics, Monduzzi Editore; pp. 33-39; (Sep. 1999).

Mageras, G.S., "Interventional Strategies for Reducing Respiratory-Induced Motion in External Beam Therapy"; The Use of Computers in Radiation Therapy X111th International Conference, Heidelberg, Germany; pp. 514-516; (May 2000).

Mah, D. et al.; "Technical Aspects of the Deep Inspiration Breath Hold Technique in the Treatment of Thoracic Cancer"; Int. J. Radiat. Oncol., Bioi., Phys. 48; pp. 1175-1185; (Nov. 2000).

Mah, K. et al.; "Time Varying Dose Due to Respiratory Motion During Radiation Therapy of the Thorax"; Proceedings of the Eighth Inl'l Conference on the Use of Computers in Radiation Therapy, Toronto, Canada; Jul. 9-12, 1984; 00. 294-298.

Malone, S. et al.; "Respiratory-Induced Prostate Motion: Quantification and Characterization", Int. J. Radial. Oneal., Bioi., Phys. 48; pp. 105-109; (Aug. 2000).

Manke, D. et al. "Model Evaluation and Calibration for Prospective Respiratory Motion Correction in Coronary MR Angiography Based on 3-D Image Registration" IEEE Transactions on Medical Imaging (Sep. 2002) 21(9):1132-1141.

Manke, D. et al. "Respiratory Motion in Coronary Magnetic Resonance Angiography: A Comparison of Different Motion Models" J. Magnetic Resonance Imaging (2002) 15:661-671.

McConnell, M.V. et al. "Comparison of Respiratory Suppression Methods and Navigator Locations for MR Coronary Angiography" AJR (May 1997) 168:1369-1375.

McConnell, M.V. et al. "Prospective Adaptive Navigator Correction for Breath-Hold MR Coronary Angiography" MRM (1997) 37:148-152.

Moerland, M.A. et al.; "The Influence of Respiration Induced Motion of the Kidneys on the Accuracy of CZ Radiotherapy Treatment Planning, A Magnetic Resonance Imaging Study", Radiotherapy Oncol. 30, pp. 150-154 (1994).

Mori, M. et al.; "Accurate Contiguous Sections Without Breath-Holding on Chest CT; Value of Respiratory Gating and Ultrafast CT"; AJR:162. May 1994; pp. 1057-1062.

Mostafavi, H.; "Method and System for Radiation Application"; U.S. Appl. No. 10/678,741, filed Oct. 3, 2003; Specification 63 pgs.; Claims 9 pgs; Abstract 1 pg; Drawings 22 pgs.

Mostafavi, Hassan; "Overview of Post-Processing Algorithm to Create Volumetric Motion Sequences"; Varian Medical Systems, Inc.; May 2, 2002; 1 page.

Nevatia, R. et. Al. "Human Body Tracking with Articulated Human Body Model" (Nov. 2002) pp. 1-3.

Nikolaou, K. et al. "Navigator Echo-Based Respiratory Gating for Three-Dimensional MR Coronary Angiography: Reduction of Scan Time Using a Slice Interpolation Technique" J. Computer Assisted Tomography (2001) 25(3):378-387.

Ohara, K. et al.; "Irradiation Synchronized With Respiration Gate"; Int. J. Radial. Oncol., Biol. Phys. 17; pp. 853-857; (Oct. 1989).

Oshinski, J.N. et al.; "Two-Dimensional Coronary MR Angiography Without Breath Holding"; Radiology 201; pp. 737-743; (Dec. 1996).

Paradis, A.L. et al. "Detection of Periodic Signals in Brain Echo-Planar Functional Images" IEEE (Jan. 1, 1997) pp. 696-697.

Peltola, Seppo M.Sc.; "Gated Radiotherapy to Compensate for Patient Breathing"; Proceedings of the Eleventh Varian Users Meeting; Macro Island, Florida; May 11•13, 1986; 4 pages.

Plein, S. et al. "Three-Dimensional Coronary MR Angiography Performed with Subject-Specific Cardiac Acquisition Windows and Motion-Adapted Respiratory Gating" AJR (Feb. 2003) 180:505-512.

Post, J.C. et al. "Three-Dimensional Respiratory-Gated MR Angiography of Coronary Arteries: Comparison with Conventional Coronary Angiography" AJR (Jun. 1996) 166:1399-1404.

Ramsey, C.R. et al.; "Clinical Efficacy of Respiratory Gated Conformal Radiation Therapy", Medical Dosimetry 24; pp. 115-119: (1999).

Ramsey, C.R. et al.;"A Comparison of Beam Characteristics for Gated and Nongated Clinical X-Ray Beams"; Med. Phys. 26; pp. 2086-2091; (Oct. 1999).

Regenfus, M. et al. "Comparison of Contrast-Enhanced Breath-Hold and Free-Breathing Respiratory-Gated Imaging in Three-dimensional Magnetic Resonance Coronary Angiography" Am. J. Cardiology (Oct. 1, 2002) 90:725-730.

Ritchie, C. J., et al.; "Predictive Respiratory Gating: A New Method to Reduce Motion Artifacts on CT Scans"; Radiology; 1994; pp. 847-852; vol. 190; No. 3.

Robinson, Terry E., et al.; "Standardized High-Resolution CT of the Lung Using a Spirometer-Triggered Electron Beam CT Scanner"; AJR:172; Jun. 1999; pp. 1636-1638.

Rogus, R.D. et al.; "Accuracy of a Photogrammetry-Based Patient Positioning and Monitoring System for Radiation Therapy"; Med. Phys. 26; pp. 721-728; (May 1999).

(56) References Cited

OTHER PUBLICATIONS

Rosenzweig, K.E. et al.; "The Deep Inspiration Breath Hold Technique in the Treatment of Inoperable Non-Small-Cell Lung Cancer"; Inl. J. Radiat. Oncol., Biol.. Phys. 48; pp. 81-87; (Aug. 2000).
Ross, C.S. et al.; "Analysis of Movement of Intrathoracic Neoplasms Using Ultrafast Computerized Tomography"; Int. J. Radia/. Oncol., Bioi., Phys. 18; pp. 671-677; (Mar. 1990).
Runge, V.M. et al.; "Respiratory Gating in Magnetic Resonance Imaging at 0.5 Tesla"; Radiology 151; pp. 521-523; (May 1984).
Sachs, T.S. et al.; "Real-Time Motion Detection in Spiral MRI Using Navigators", Magn. Reson. Med. 32; pp. 639-645; (Nov. 1994).
Schar, M. et al. "The Impact of Spatial Resolution and Respiratory Motion on MR Imaging of Atherosclerotic Plaque" J. Magnetic Resonance Imaging (2003) 17:538-544.
Schwartz, L.H. et al.; "Kidney Mobility During Respiration"; Radio/her. Oncol. 32; pp. 84-86; (1994).
Shirato, H. et al.; "Four-Dimensional Treatment Planning and Fluroscopic Real-Time Tumor Tracking Radiotherapy for Moving Rumor"; Int. J. Radial. Oncol., Bioi., Phys. 48; pp. 435-442; (Sep. 2000).
Sinkus, Ralph. et al.; "Motion Pattern Adapted Real-Time Respiratory Gating"; Magnetic Resonance in Medicine 41; 1999; pp. 148-155.
Solberg, Timothy D., et al.; "Feasibility of Gated IMRT"; Proceedings of the 22nd Annual International Conference of the IEEE Engineering in Medicine and Biology Society, Chicago, IL (Jul. 23-28, 2000) 3pps: 2732-2734.
Spuentrup, E. et al. "Respiratory motion artifact suppression in diffusion-weighted MR imaging of the spine" Eur. Radiol. (2003) 13:330-336.
Suramo, M.P. et al.; "Cranio-caudal Movements of the Liver, Pancreas and Kidneys on Respiration", Acta Radiol. Diagn. 2; pp. 129-131; (1984).
Tada, Takuhito, et al.; "Lung Cancer: Intermittent Irradiation Synchronized With Respiratory Motion-Results of a Pilot Study"; Radiology, Jun. 1998; vol. 207; No. 3; pp. 779-783.
Thickman, D. et al. "Phase-Encoding Direction upon Magnetic Resonance Image Quality of the Heart" Magnetic Resonance in Medicine (1988) 6:390-396.
van Geuns, R.J.M. et al.; "Magnetic Resonance Imaging of the Coronary Arteries: Clinical Results From ThreeDimensional Evaluation of a Respiratory Gated Technique"; Heart 82; pp. 515-519; (Oct. 1999).
Wang, Y. et al. "Navigator-Echo-based Real-Time Respiratory Gating and Triggering for Reduction of Respiration Effects in Three-dimensional Crornary MR Angiography" Radiology (1996) 198:55-60.
Wang, Y. et al.; "Implications for the Spatial Resolution in Coronary Imaging"; Magnetic Resonance in Medicine 33; 1995; pp. 713-719.
Weber, C. et al. "Correlation of 3D MR coronary angiography with selective coronary angiography: feasibilitly of the motion adapted gating technique" Eur. Radiol. (2002) 12:718-726.
Weiger, Markus, et al.; "Motion-Adapted Gating Based on k-Space Weighting for Reduction of Respiratory Motion Artifacts"; Magnetic Resonance in Medicine 38; 1997; pp. 322-333.
Wiesmann, F. "High-Resoulution MRI with Cardiac and Respiratory Gating Allows for Accurate in Vivo Atherosclerotic Plaque Visualization in the Muring Aortic Arch" Magnetic Resonance in Medicine (2003) 50:69-74.
Wong, J.W. et al.; "The Use of Active Breathing Control (ABC) to Reduce Margin for Breathing Motion"; In/. J.Radial. Oncol., Phys. 44; pp. 911-919; (Jul. 1999).
Wood, M. L. and R. M. Henkelman "Suppression of respiratory motion artifacts in magnetic resonance imaging" Med. Phys. (Nov./Dec. 1996) 13(6):794-805.
Woodard, P.K., et al.; "Detection of Coronary Stenoses on Source and Projection Images Using Three-Dimensional MR Angiography With Retrospective Respiratory Gating: Preliminary Experience"; AJR:170; Apr. 1998; No. 4; 00. 883-888.

Worthley, S.G. et al. "Cardiac gated breath-hold back blood MRI of the coronary artery wall: An in vivo and ex-vivo comparison" Int'l J. Cardiovascular Imaging (2001) 17:195-201.
Yamashita, Y. et al. "MR Imaging of Focal Lung Lesions: Elimination of Flow and Motion Artifact by Breath-Hold ECG-Gated and Black-Blood Techniques on T2-Weighted Turbo SE and STIR Swquences" J. Magnetic Resonance Imaging (1999) 9:691-698.
Yorke, E. et al.; "Respiratory Gating of Sliding Window IMRT"; 22nd Annual EMBS International Conference. Chicago, IL.; pp. 2118-2121; (Jul. 23-28, 2000).
Yuan, Q. et al.; "Cardiac-Respiratory Gating Method for Magnetic Resonance Imaging of the Heart"; Magn. Reson. Med. 43; pp. 314-318; (Feb. 2000).
Vedam, S.S. et al., "Acquiring a four-dimensional computed tomography dataset using an external respiratory signal" Phys. Med. Bio. 48 (2003), pp. 45-62.
International Search Report and Written Opinion dated Feb. 5, 2007 for PCT/US2005/034999.
International Search Report and Written Opinion dated Dec. 1, 2005 (PCT/US05/08037).
International Search Report and Written Opinion dated Oct. 13, 2005 (PCT/US04/32381).
International Search Report, Varian Medical Systems, Inc. PCT/US03/27552, Feb. 19, 2004.
Preliminary Search Brochure entitled "Kinematic Measurement Systems" by Qualisys printed Apr. 4, 1994; 4 pages.
International Search Report for PCT/US03/36454 issued May 28, 2004.
International Search Report and Written Opinion dated Feb. 15, 2005 for PCT/US2004/029277.
International Search Report and Written Opinion dated Jan. 30, 2006 for PCT/US2004/028571.
International Search Report and Written Opinion dated Mar. 15, 2005 for PCT/US2004/028756.
Wang, Y. et al. "Respiratory Motion of the Heart: Kinematics and the Implication for the Spatial Resolution in Coronary Imaging" Magnetic Resonance in Medicine (1995) 33:713-719.
Non Final Office Action dated Aug. 4, 2009 for U.S. Appl. No. 10/678,741.
Non Final Office Action dated Aug. 19, 2008 for U.S. Appl. No. 10/678,741.
Non Final Office Action dated Jan. 16, 2008 for U.S. Appl. No. 10/678,741.
Final Office Action dated Feb. 17, 2009 for U.S. Appl. No. 10/678,741.
Non Final Office Action dated Aug. 21, 2009 for U.S. Appl. No. 11/116,699.
Non Final Office Action dated Apr. 3, 2009 for U.S. Appl. No. 12/182,932.
Final Office Action dated Nov. 3, 2009 for U.S. Appl. No. 12/182,932.
Non Final Office Action dated Nov. 21, 2008 for U.S. Appl. No. 10/656,478.
Non Final Office Action dated May 20, 2008 for U.S. Appl. No. 10/656,478.
Non Final Office Action dated Jun. 13, 2007 for U.S. Appl. No. 10/656,478.
Non Final Office Action dated Dec. 13, 2006 for U.S. Appl. No. 10/656,478.
Final Office Action dated May 5, 2009 for U.S. Appl. No. 10/656,478.
Final Office Action dated Nov. 5, 2007 for U.S. Appl. No. 10/656,478.
Non Final Office Action dated Jan. 26, 2010 for U.S. Appl. No. 10/656,478.
Non Final Office Action dated Mar. 4, 2010 for U.S. Appl. No. 11/116,699.
Non Final Office Action dated Jul. 7, 2010 for U.S. Appl. No. 10/678,741.
Non-Final Office Action dated Sep. 14, 2010 for U.S. Appl. No. 11/116,699.
Final Office Action dated Aug. 5, 2010 for U.S. Appl. No. 10/656,478.

(56) References Cited

OTHER PUBLICATIONS

Final Office Action dated Dec. 8, 2010 for U.S. Appl. No. 10/678,741.
Final Office Action dated Feb. 28, 2011 for U.S. Appl. No. 11/116,699.
Adler Jr. et al., "Image-Guided Robotic Radiosurgery". Neurosurgery, vol. 44, No. 6, Jun. 1999.
Murphy et al., "Patterns of Patient Movement During Frameless Image-Guided Radiosurgery". International Journal of Radiation Oncology Biology Physics, vol. 55, No. 5, Apr. 1, 2003.
Neicu et al., "Synchronized Moving Aperture Radiation Therapy (SMART): Average Tumour Trajectory for Lung Patients". Physics in Medicine and Biology, vol. 48, No. 5, Narch 7, 2003.
European Supplementary Search Report for EP Application No. 04783114.4 mailed Dec. 30, 2010.
Final Office Action dated Jan. 27, 2012 for U.S. Appl. No. 10/678,741.
Advisory Action dated Apr. 20, 2012 for U.S. Appl. No. 10/678,741.
Japanese Notice of Reasons for Refusal Dated Jan. 5, 2012 for JP Application No. 2006-525439.
Japanese Notice of Reasons for Refusal Dated Jul. 25, 2011 for JP Application No. 2006-525439.
Japanese Notice of Reasons for Refusal Dated Aug. 9, 2010 for JP Application No. 2006-525439.
European Office Action Dated Mar. 12, 2012 for EP Application 04782961.9.
European Office Action Dated Apr. 21, 2010 for EP Application 04782961.9.
European Office Action Dated Mar. 29, 2011 for EP Application 04782961.9.
European Office Action Dated Sep. 7, 2010 for EP Application 04782961.9.
European Office Action Dated Apr. 28, 2011 for EP Application 04783114.4.
Japanese Decision to Dismiss the Amendment Dated Aug. 31, 2011 for JP Application 2006-526196.
Japanese Notice of Reason for Refusal Dated Feb. 21, 2011 for JP Application 2006-526196.
Japanese Notice of Reason for Refusal Dated Aug. 3, 2010 for JP Application 2006-526196.
Japanese Notice of Reason for Refusal Dated Apr. 7, 2010 for JP Application 2006-526196.
European Office Action Dated Aug. 21, 2009 for EP Application 04793980.6.
European Office Action Dated Mar. 8, 2011 for EP Application 04793980.6.
European Office Action Dated Oct. 7, 2010 for EP Application 04783505.3.
European Supplementary Search Report Dated Jun. 16, 2010 for EP Application 04783505.3.
Japanese Notice of Reason for Refusal Dated Oct. 6, 2009 for JP Application 2006-525540.
Japanese Notice of Reason for Refusal Dated Mar. 17, 2010 for JP Application 2006-525540.
Japanese Notice of Reason for Refusal Dated Mar. 22, 2011 for JP Application 2006-525540.
Japanese Decision of Refusal Dated Apr. 21, 2009 for JP Application 2003-509826.
Notice of Questioning for Shimpan Appeal Dated Apr. 26, 2010 for JP Application 2003-509826.
Non-Final Office Action dated Apr. 17, 2012 for U.S. Appl. No. 12/205,431.
European Supplementary Search Report for EP Application No. 04793980.6 mailed Mar. 12, 2009.
English Abstract for Foreign Application No. JP 6-292085.
English Abstract for Foreign Application No. JP 7-275237.
English Abstract for Foreign Application No. JP 10-289321.
Non-Final Office Action dated Oct. 24, 2011 for U.S. Appl. No. 12/205,512.
Final Office Action dated Dec. 16, 2011 for U.S. Appl. No. 12/182,932.
Non-Final Office Action dated Aug. 12, 2011 for U.S. Appl. No. 12/182,932.
Non-Final Office Action dated Jul. 20, 2011 for U.S. Appl. No. 10/678,741.
Final Office Action dated Sep. 4, 2012, for U.S. Appl. No. 12/205,512.
Advisory Action dated Nov. 9, 2012, for U.S. Appl. No. 12/205,512.
Final Office Action dated Nov. 7, 2012, for U.S. Appl. No. 12/182,932.
Final Office Action dated Dec. 19, 2012, for U.S. Appl. No. 10/656,478.
Notice of Reasons for Refusal dated Dec. 17, 2012 for Japanese Patent Application No. 2011-25872.
Office Action dated Nov. 7, 2012 for European Patent Application No. 04783114.4.
Final Office Action dated Oct. 11, 2012, for U.S. Appl. No. 12/205,431.
Japanese Notice of Questioning for Shimpan Appeal dated Sep. 12, 2012, for JP Application No. 2006-526196.
English Translation of Japanese Notice of Questioning for Shimpan Appeal dated Sep. 12, 2012, for JP Application No. 2006-526196.
Bifulco P et al., "Automatic Recognition of Vertebral Landmarks in Fluoroscopic Sequences for Analysis of Intervertebral Kinematics", Medical and Biological Engineering and Computing, Springer, Heildelberg, DE, vol. 39, No. 1, Jan. 1, 2011, 12 pages.
Eisner R L et al., "Use of Cross-Correlation Function to Detect Patient Motion During Spect Imaging", Journal of Nuclear Medicine, Society of Nuclear Medicine, Reston, VA, US, vol. 28, No. 1, Jan. 1, 1987, 6 pages.
European Office Action Dated Jun. 14, 2012 for EP Application No. 04793980.6.
European Search Report and Opinion Dated May 24, 2012 for EP Application No. 12164387.8.
European Office Action dated Jun. 5, 2012 for EP Application No. 04783114.4.
Advisory Action dated Jan. 9, 2013 for U.S. Appl. No. 12/205,431.
Notice of Reasons for Refusal dated Feb. 12, 2013 for JP Patent Application No. 2006-526196.
Translation of Notice of Reasons for Refusal dated Feb. 12, 2013 for JP Patent Application No. 2006-526196.
First Examination Report dated Feb. 21, 2013 for EP Patent Application No. 12 164 387.8.
Non-final Office Action dated May 31, 2013 for U.S. Appl. No. 10/678,741.
Notice of Reasons for Refusal dated Apr. 10, 2013, for JP Patent Application No. 2011-025872.
English Translation of Notice of Reasons for Refusal dated Apr. 10, 2013 for JP Patent Application No. 2011-025872.
Office Action dated Aug. 2, 2013 for EP Patent Application No. 04793980.6, 4 pages.
E.C. Ford et al., "Respiration-correlated spiral CT: A method of measuring respiratory-induced anatomic motion for radiation treatment planning" Med. Phys. 30 (1), Jun. 13, 2002, 12 pages.

* cited by examiner

SYSTEMS AND METHODS FOR GATING MEDICAL PROCEDURES

BACKGROUND OF THE INVENTION

1. Field of the Invention

The field of the invention relates to medical methods and systems, and more particularly, to systems and methods for gating medical procedures.

2. Background of the Invention

Radiation therapy involves medical procedures that selectively expose certain areas of a human body, such as cancerous tumors, to doses of radiation. The purpose of the radiation therapy is to irradiate the targeted biological tissue such that undesirable tissue is destroyed. Radiation has also been used to obtain image of tissue for diagnostic or treatment purposes.

In a radiation treatment session, the position and movement of a target tissue can be monitored by an imaging system, such as a fluoroscopic imaging system, while radiation is delivered to the target tissue. This ensures that the target tissue is in a desired position while the radiation is being delivered. However, often soft tissue targets such as a variety of tumors are not visible in x-ray fluoroscopic images. This is due to structures in front or behind the target tissue which are also visible in the x-ray images thus increasing the clutter to the level that the target tissue cannot be distinguished.

Internal radio-opaque markers have been used to aid physicians in identifying a target tissue under fluoroscopic imaging. The radio-opaque markers can be injected or implanted at desired sites within a patient, and they shows up as high contrast features in fluoroscopic images. By observing the positions of the internal radio-opaque markers in fluoroscopic images, a physician can determine a position of a target tissue. However, implantation of markers is intrusive to the patient, and it may not be practical or feasible in all cases.

Accordingly, systems and methods for gating medical procedures without use of internal markers would be useful.

SUMMARY OF THE INVENTION

In accordance with an embodiment of the invention, a method of gating a medical procedure is provided. The method includes acquiring a first image of a target region, acquiring a second image of the target region, determining a composite image based on the first and second images, and gating a medical procedure based on the composite image. In one embodiment, the composite image may be determined by subtracting the first image from the second image. By observing the contrast of the composite image, a degree of detected motion of the target region may be determined. For example, a value associated with a contrast of the composite image may be determined, and a medical procedure may then be gated based on the value. With respect to radiation therapy, a radiation beam may be deactivated when the value associated with the contrast of the composite image exceeds a certain prescribed threshold. Such method does not require the use of markers, and can easily be implemented using existing imaging systems.

In accordance with another embodiment of the invention, a method of gating a medical procedure includes providing a template, acquiring an input image of a target region, registering the input image with the template, determining a position of the target region based on the registering, and gating a medical procedure based on the determined position of the target region. In one embodiment, the template is selected from a plurality of templates, each of which has an image. The registering the input image with one of the templates includes selecting a template from the plurality of templates that best matches at least a portion of the input image. The method has applications in a wide range of medical procedures. By means of non-limiting example, the method may be used to gate an activation of a radiation beam directed towards a tissue.

In accordance with yet another embodiment of the invention, a method of performing a medical procedure includes providing a plurality of templates, each of which having an image and treatment data, acquiring an input image, registering the input image with one of the templates, and performing a medical procedure based on the treatment data of the one of the templates that is registered with the input image. In one embodiment, the registering the input image with one of the templates includes selecting a template from the plurality of templates that best matches at least a portion of the input image. By means of non-limiting example, the treatment data may include radiation treatment data, such as beam shape data, beam-on data, beam-off data, and/or beam-on duration data. In this case, when the input image is registered with a template, a treatment radiation source may direct a treatment radiation beam towards a target region based on the treatment data prescribed by the corresponding template.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting its scope, the invention will be described and explained with additional specificity and detail through the use of the accompanying drawings.

DETAILED DESCRIPTION OF THE PREFERRED EMBODIMENTS

Figure 1:
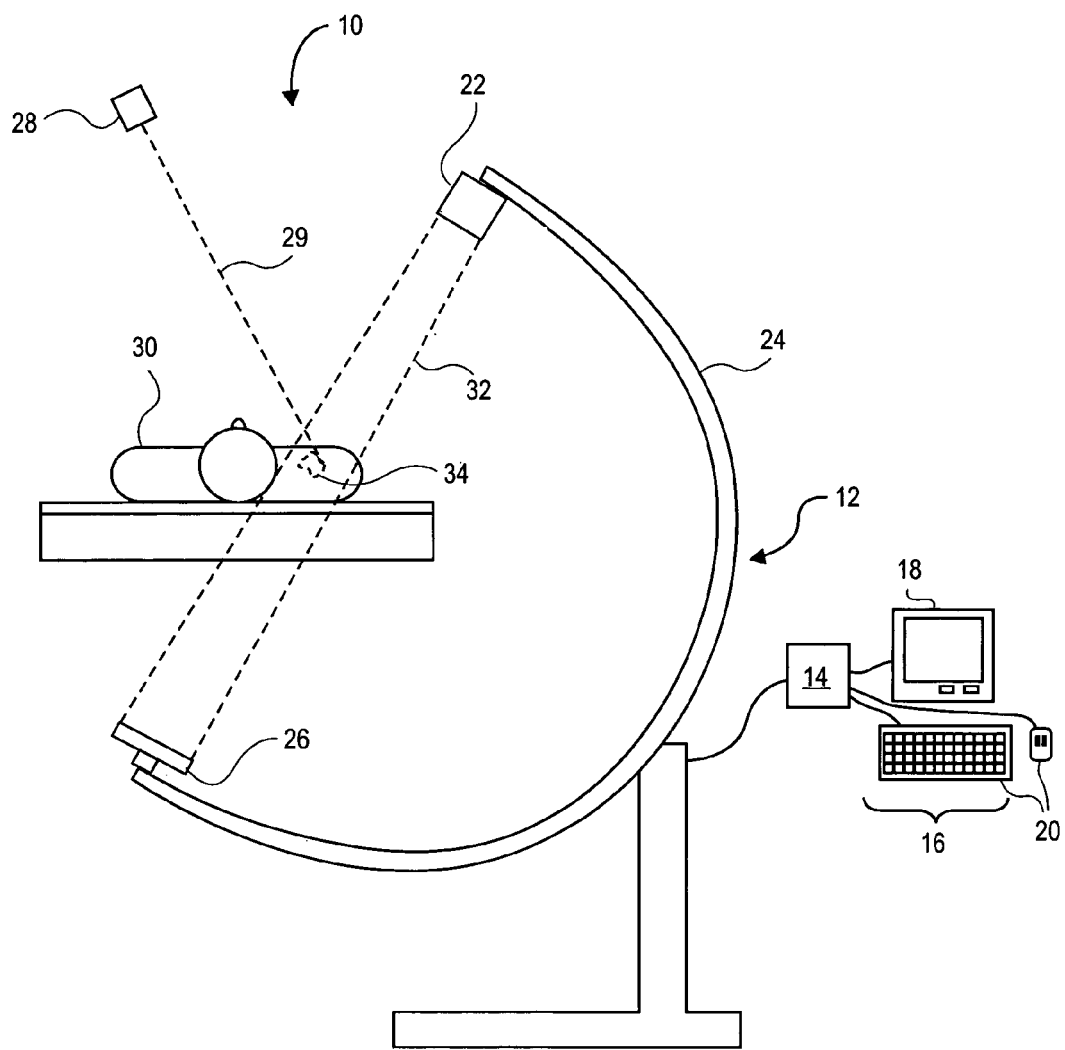
FIG. 1 illustrates a fluoroscopic imaging system with which embodiments of the present invention may be implemented.

Various embodiments of the present invention are described hereinafter with reference to the figures. It should be noted that the figures are not drawn to scale and that elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an illustrated embodiment needs not have all the aspects or advantages of the invention shown. An aspect or an advantage described in conjunction with a particular embodiment of the present invention is not necessarily limited to that embodiment and can be practiced in any other embodiments of the present invention even if not so illustrated.

FIG. 1 illustrates a fluoroscopic system 10 with which embodiments of the present invention may be implemented. The system 10 includes a fluoroscope 12, a processor 14, and a work station 16 having a display 18 and a user interface 20, such as a keyboard and/or a mouse. The processor 14 may be an integral component of the work station 16, or alternative, a separate component that is connected to the work station 16. The fluoroscope 12 is illustrated as a C-arm fluoroscope in which an x-ray source 22 is mounted on a structural member or C-arm 24 opposite to an imaging assembly 26, which is configured to receive and detect x-ray emitting from the x-ray source 22. The C-arm 24 is capable of moving about a patient for producing two dimensional projection images of the patient from different angles.

During use of the fluoroscopic system 10, a patient 30 is positioned between the x-ray source 22 and the imaging assembly 26. A x-ray beam 32 is then directed towards a target region 34 within the patient 30, and is attenuated as it passes through the patient 30. The imaging assembly 26 receives the attenuated x-ray beam 32, and generates electrical signals in response thereto. The electrical signals are transmitted to the processor 14, which is configured to generate images in the display 18 based on the electrical signals in accordance with an embodiment of the present invention. During a treatment session, another radiation source 28 may be positioned adjacent the fluoroscopic system 10 for delivering treatment radiation 29 to the target region 34. Similar imaging systems or other types of imaging systems may also be used to implement embodiments of the present invention.

Figure 2:
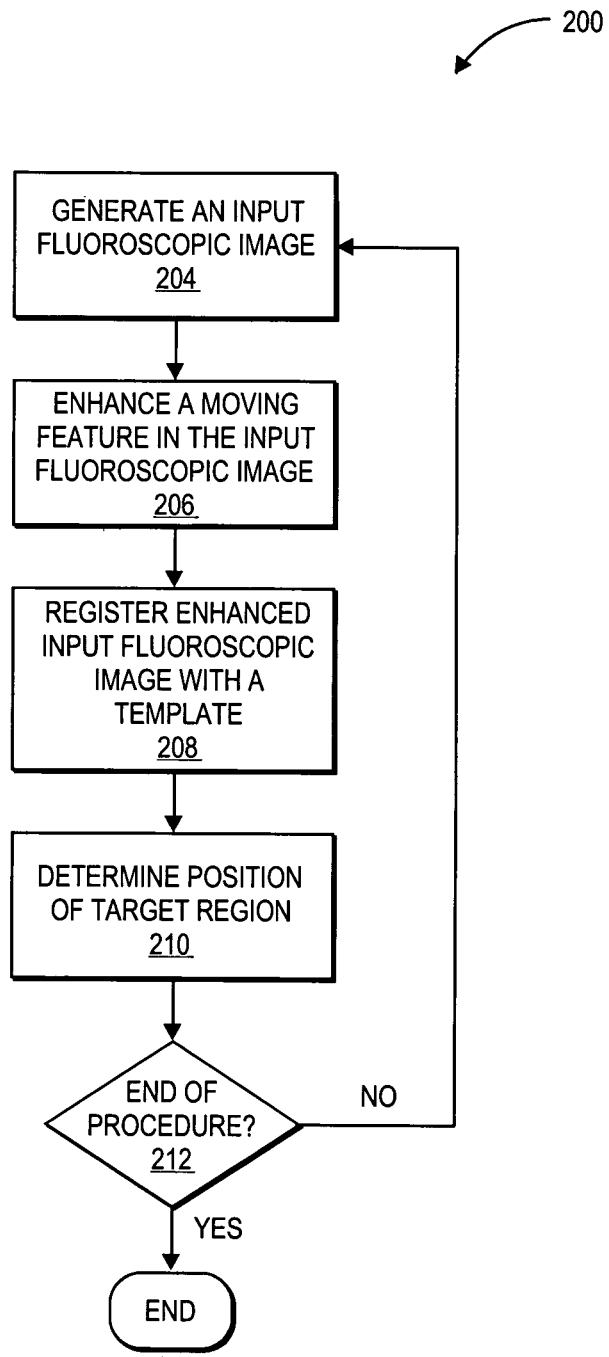
FIG. 2 is a flowchart showing a process for targeting an object in accordance with an embodiment of the invention.

FIG. 2 is a block diagram illustrating an embodiment of a process 200 for tracking a position of the target region 34 of the patient 30 as the target region 34 is being imaged using the fluoroscopic system 10 of FIG. 1.

To track a position of the target region 34 of the patient 30 undergoing a fluoroscopic imaging, a real-time input fluoroscopic image is generated using the fluoroscopic system 10 (Step 204). The target region 34 may include a tissue, such as a lung tissue or a heart tissue, that undergoes periodic physiological movements. Alternatively, the target region 34 may also include tissue that does not undergoes periodic physiological movements, such as a bone tissue or prostate.

Next, the processor 14 processes the fluoroscopic image to enhance a feature, such as a moving feature of an object, in the fluoroscopic image (Step 206). By enhancing a moving feature in the input fluoroscopic image, contrast of an image of a moving object is enhanced while contrast of an image of a relatively stationary object is reduced. In the illustrated embodiment, the enhancement of the moving feature may be performed based on image averaging and image subtraction techniques.

In one embodiment, boxcar averaging technique may be used. Particularly, to obtain an enhanced input fluoroscopic image $EIFI_n$ for the nth input fluoroscopic image $IFI_n$, a long term average of the previous input fluoroscopic images is calculated and subtracted from the nth input fluoroscopic image $IFI_n$, (i.e., $EIFI_n = IFI_n - Avg(IFI_{x=n-m \ to \ x=n-1}$, where m=length of boxcar). For example, the sixth input fluoroscopic image $IRFI_6$ may be enhanced or modified by performing image averaging on the previous five input fluoroscopic images to obtain a composite image (i.e. an average image), and by subtracting the composite image from the sixth input fluoroscopic image $RFI_6$. As used in this specification, the term "composite image" includes an array of data that may be stored in a medium, and therefore, is not limited to a displayed image.

Figure 3:
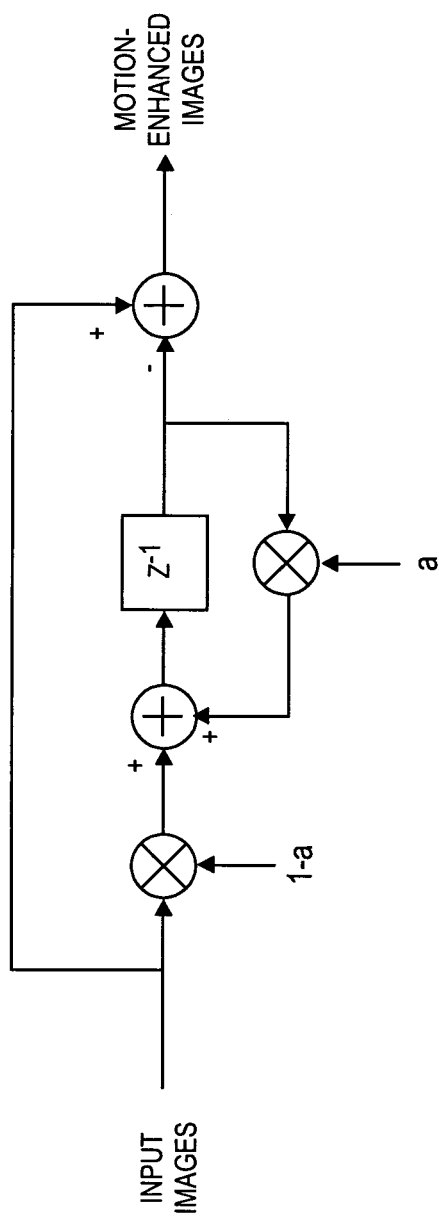
FIG. 3 shows an algorithm for processing images in accordance with an embodiment of the invention.

In an alternative embodiment, the image averaging may be performed based on a weighted average prescribed as a function over time. For example, if later input fluoroscopic images are to be accounted for more in the averaging, later input fluoroscopic images may be multiplied by a higher weighted factor during the image averaging, and vice versa. FIG. 3 shows a recursive algorithm for enhancing a moving feature of an object in an image, in which the current input fluoroscopic image is multiplied by a weighted factor (1-a) while the previous recursive average of the input fluoroscopic image(s) is multiplied by a weighted factor (a). The $Z^{-1}$ represents a memory that holds one frame with one frame time delay. This results in an exponentially decreasing weighted average for the earlier samples. Other types of weighted averaging may also be used.

It should be noted that the process of enhancing a feature in the fluoroscopic image is not limited to the examples described previously, and that other modified versions of the process may also be used. For example, in another embodiment, the boxcar averaging may be performed on certain previous input fluoroscopic images (e.g., the last three images), instead of on all of the previous input fluoroscopic images. In other embodiments, other functions or algorithms may be applied to any combination of the previous input fluoroscopic images and/or the current input fluoroscopic image before or after the image averaging is performed.

The processor 14 next registers the enhanced input fluoroscopic image with a template (Step 208). In the illustrated embodiment, a sequence of templates is provided, and each of the templates contains an image of at least a portion of the target region 34 that is created at a certain time-point or a phase of a physiological cycle. The processor 14 selects a template from the sequence of templates that best matches an image of the target region 34 in the enhanced input fluoroscopic image. The construction of the templates will be described later. As used in this specification, the term "phase" refers to a variable that represents, measures, or associates with, a degree of completion of a physiological cycle.

In one embodiment, the input fluoroscopic image is compared with the templates, and the template that best matches with an image in the input fluoroscopic image is registered or cross correlated with the input fluoroscopic image. In this case, the processor 14 performs an image comparison to determine which portion of the enhanced input fluoroscopic image best matches with each of the template images. Known techniques for performing image analysis, such as pattern matching, may be used. For example, if a template contains an image formed by 50×50 pixels, the processor 14 may perform a spatial analysis to determine a region (having 50×50 pixels) within the enhanced input fluoroscopic image that best matches the template image. The processor 14 then computes values representative degrees of match between the templates and an image in the input fluoroscopic image, and selects the template associated with the highest value to be registered with the input fluoroscopic image. The position of the image within the input fluoroscopic image that best matches the registered template may be stored in a computer-readable medium for later use.

In one embodiment, each cross correlation between the enhanced input image and a template results in a 2D correlation function with a correlation peak. In each correlation function, the location of the peak indicates the position of the target region 34, and the value of the peak indicates a degree of match between the input fluoroscopic image and the template. The template that provides the highest peak value is then selected as the matching template, and the corresponding peak position in the correlation function is used to determine the position of the target region 34.

Examples of an algorithm that may be used to search for the template that best matches the input fluoroscopic image will now be described. However, it should be understood that the determination of the template that best matches the input fluoroscopic image may also be performed using other algorithms or techniques. In one embodiment, the input fluoroscopic image is compared with all of the templates to determine the matching template. In another embodiment, instead of comparing the input fluoroscopic image with all of the templates, the input fluoroscopic image is compared with only a subset of templates. In this case, the subset of templates are selected such that their corresponding phase values (or time points of a respiration cycle at which they are generated) are centered around, or proximate to, the phase of the template that had the best match with the last input fluoroscopic image (i.e., from the last tracking cycle). Such technique increases the efficiency for registering the input fluoroscopic image with the template because an input fluoroscopic image and a template that are collected at the same phase or time-point of a physiological cycle are likely to have similar image contrast. In another embodiment, if a match is found between the previous input fluoroscopic image and a template, and if the templates and the fluoroscopic images are generated at substantially the same phases or time-points of a physiological cycle, the next template in the sequence may be selected to determine if it matches with an image in the current input fluoroscopic image. If it is determined that the template does not match the input fluoroscopic image (i.e., the degree of match does not exceed a prescribed threshold), another template is then selected to determine if it matches with an image in the input fluoroscopic image. For example, the next template or the previous template in the sequence may be selected, until a match is found.

Once the input fluoroscopic image is matched with the template, the position of the target region 34 in the fluoroscopic image is determined (Step 210). Particularly, the position of the image in the input fluoroscopic image that matches with the template is the position of the target region 34. A marker may be displayed in the display 18 to indicate the position of the identified target region 34 in the input fluoroscopic image. For example, a frame or an outline having a similar shape as that of the corresponding registered template may be displayed in the input fluoroscopic image. The phase associated with the input fluoroscopic image can be determined based on the phase of the matched template. Alternatively the phase associated with the input fluoroscopic image can be determined by a separate tracking mechanism, such as RPM external markers, available at Varian Medical System, Inc., Palo Alto, Calif.

The next real-time input fluoroscopic image is generated and the previously described process is repeated until the end of the session is reached (Step 212). The templates and the input fluoroscopic images may be generated at same or different time intervals. For example, the templates may be generated at a shorter time interval as compared to that for the input fluoroscopic images, thereby allowing more matching variations between different sets of the input fluoroscopic images and the templates.

It should be noted that the steps described previously with reference to the process 200 can be carried out in substantially real-time. That is, the input fluoroscopic images can be processed to determine a position of the target region immediately or shortly after they are generated in step 204. Alternatively, the input fluoroscopic images can be generated in a batch, time-stamped, and stored for subsequent processing. In this case, the enhancing step 206, the registering step 208, and the determining step 210 can be performed subsequently.

Figure 4:
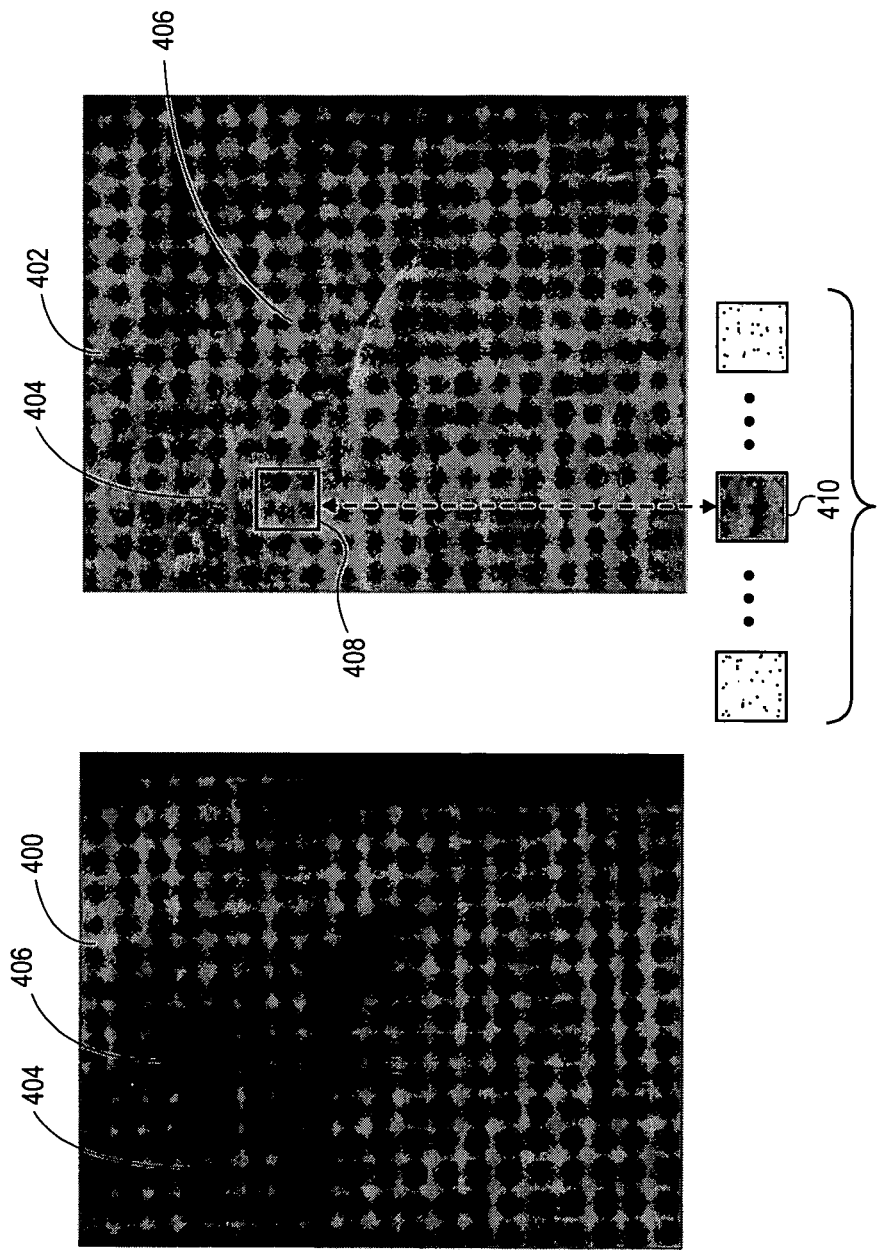
FIG. 4 shows examples of images generated during a treatment or diagnostic session performed in accordance with the process of FIG. 2.

FIG. 4 shows examples of images generated at different stages of the dynamic targeting process described previously. An example of an input fluoroscopic image 400 created during a phase of a respiratory cycle, and its corresponding motion enhanced fluoroscopic image 402 created using the technique described with reference to step 206 are shown. As can be seen in the figure, by subtracting the average image from the current input fluoroscopic image, the moving object(s), i.e., the lung tissue 404, is enhanced while the contrast of the relatively stationary object(s), i.e., the bone 406, is reduced. FIG. 4 also shows a rectangular frame 408 displayed in the fluoroscopic image 402 identifying a region in the fluoroscopic image 402 that matches with the template 410. The template 410 is selected from a group 412 of available templates. The group 412 can include all of the generated templates, or alternatively, a subset of the generated templates, as discussed previously.

Figure 5:
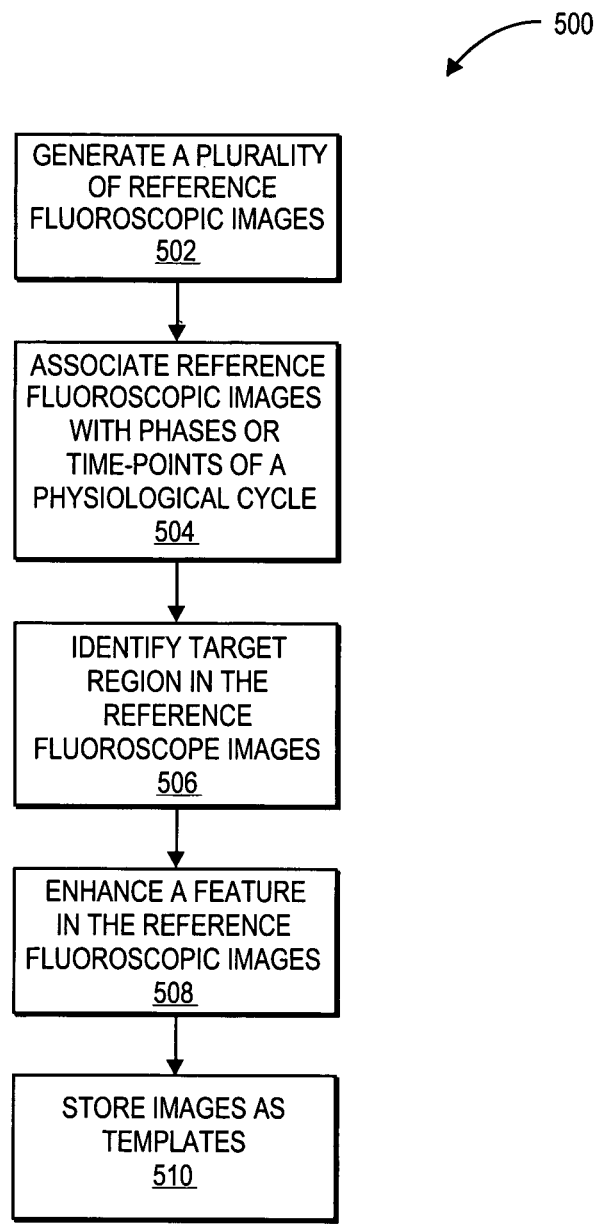
FIG. 5 is a flowchart showing a process for generating templates that may be used in the process of FIG. 2.

The construction of the templates will now be described. Various methods may be used to generate the templates. FIG. 5 shows a process 500 for generating the sequence of templates in accordance with an embodiment of the present invention. First, the radiation source 22 of the fluoroscopic system 10 is positioned and aimed towards an area of the body that includes the target region 34, and a plurality of reference fluoroscopic images RFI is generated using the fluoroscopic system 10 (Step 502). The position and orientation of the x-ray source 22 relative to the patient 30 may be stored for later use. Particularly, the position and orientation of the x-ray source 22 used during the template generation session may be used to set up the x-ray source 22 for generating the input fluoroscopic images. As a result, the image in the input fluoroscopic image would be similar to that in the template, thereby allowing matching of the template with the input fluoroscopic image. If the target region 34 includes a moving tissue, the plurality of reference fluoroscopic images is preferably collected over a physiological cycle, such as a respiratory cycle or a cardiac cycle, of the moving tissue. In one embodiment, 120 to 200 reference fluoroscopic images are collected over a period of 12 to 20 seconds in order to capture movements of the target region 34 during a respiratory cycle. The collected reference fluoroscopic images are time-stamped and are then stored in digital format in a computer readable medium, such as a hard-drive, a CD-Rom, a diskette, or a server.

Next, the reference fluoroscopic images are associated with phases or time-points of a physiological cycle (Step 504). In one embodiment, the generated reference fluoroscopic images are time-stamped as they are generated in Step 502. A patient position monitoring system, such as that available at Varian Medical System, Inc., Palo Alto, Calif., may be used to detect physiological motion of the patient, and generates motion data as the reference fluoroscopic images are generated. The reference fluoroscopic images are then associated with phases or time-points of a physiological cycle based on their corresponding stamped time and the motion data. For example, the reference fluoroscopic images can be synchronized with the motion data to a common time line. In another embodiment, the reference fluoroscopic images may also be registered in phase with three-dimensional computed tomography images generated during a planning session (described below).

In Step 506, images of the target region 34 are identified in the respective reference fluoroscopic images. In one embodiment, the images of the target region 34 may be determined manually by a user, such as a physician or a technician. In this case, the user examines each of the selected reference fluoroscopic images and identifies the target region 34 in each of the selected reference fluoroscopic images. For each identified target region 34 in the reference fluoroscopic images, the user may place a marker representative of the position of the target region 34 in the corresponding reference fluoroscopic image. For example, the user may operate the user interface 20 and place a frame around a region of interest (ROI) containing the target region 34 in the corresponding reference fluoroscopic image. Alternatively, the user may also draw an outline around a ROI having a shape that resembles the target region 34 in the corresponding reference fluoroscopic image. In this case, the outline may represent a boundary of the target region 34 to which treatment may be applied.

In another embodiment, the image of the target region 34 in the respective reference fluoroscopic images may be determined by projecting a three-dimensional (3D) treatment volume onto the respective reference fluoroscopic images. In this case, a number of 3D computed tomography (CT) images of the treatment volume are obtained such that they cover a period, such as a physiological cycle. The 3D CT images may be generated simultaneously with the sequence of the reference fluoroscopic images. Alternatively, the 3D CT images may be generated separately from the reference fluoroscopic images, in which case, the reference fluoroscopic images may subsequently be registered in phase with the 3D CT images. Conventional techniques may be employed to register the sequence of the reference fluoroscopic images with the CT images. PRM Respiratory Gating System, available at Varian Medical System, Inc., Palo Alto, Calif., may also be used to register the reference fluoroscopic images with the CT images.

The 3D CT images are then examined to determine the position of the target region 34 in the respective images. In one embodiment, the position of the target region 34 in each of the respective CT images is projected onto the respective two-dimensional (2D) reference fluoroscopic image using known transformation techniques. Based on the projected positions of the target region 34 in the respective reference fluoroscopic images, ROIs containing images of the target region 34 can then be defined in the respective reference fluoroscopic images. For example, a rectangular frame circumscribing the target region 34 may be used to define a ROI. Alternatively, an outline having a shape that resembles the target region 34 may define a ROI.

Next, the reference fluoroscopic images are processed to enhance a moving object in the images (Step 508). The enhancement of a moving object may be performed using a similar technique described previously with reference to the input fluoroscopic images. In the illustrated embodiment, each of the reference fluoroscopic images in the sequence is modified based on image averaging and image subtraction techniques. Particularly, to obtain an enhanced reference fluoroscopic image $ERFI_n$ for the nth reference fluoroscopic image $RFI_n$ in the sequence, a long term average of the previous reference fluoroscopic images is calculated and subtracted from the nth reference fluoroscopic image $RFI_n$, (i.e., $ERFI_n = RFI_n - Avg(RFI_{x=1\ to\ x=n-1})$. For example, the sixth reference fluoroscopic image $RFI_6$ in the sequence is modified by performing image averaging on the previous five fluoroscopic images to obtain an average image, and by subtracting the average image from the sixth fluoroscopic image $RFI_6$. In one embodiment, the image averaging may be performed based on boxcar or recursive techniques. In alternative embodiments, the image averaging may be performed based on a weighted average prescribed as a function over time, as described previously.

Next, the images contained within the ROIs in the reference fluoroscopic images are stored as a sequence of templates (Step 510). The templates may be stored in a computer readable medium, such as a hard-drive, a CD-Rom, a diskette, or a server.

In the previously described embodiment, the motion enhancement is performed after the ROIs are determined in the reference fluoroscopic images. However, this needs not be the case. In an alternative embodiment, the order of the steps of enhancing a moving object and ROI determination can be different from the process 500. Furthermore, in another embodiment, instead of generating reference fluoroscopic images, digitally reconstructed radiographs (DRR) are produced from each reference 3D CT image for the direction of fluoroscopic image that will be used in treatment. In this case, the target volume is projected in each DRR, and the DRRs are used as the reference fluoroscopic images in the same manner as the previous embodiment.

It should be noted that the above-described process 500 for generating the sequence of templates may be performed in the same session (e.g., a treatment session) in which the process 200 is being performed. Alternatively, the templates may be generated in another session that is carried out separately and prior to a treatment or diagnostic session.

Figure 6:
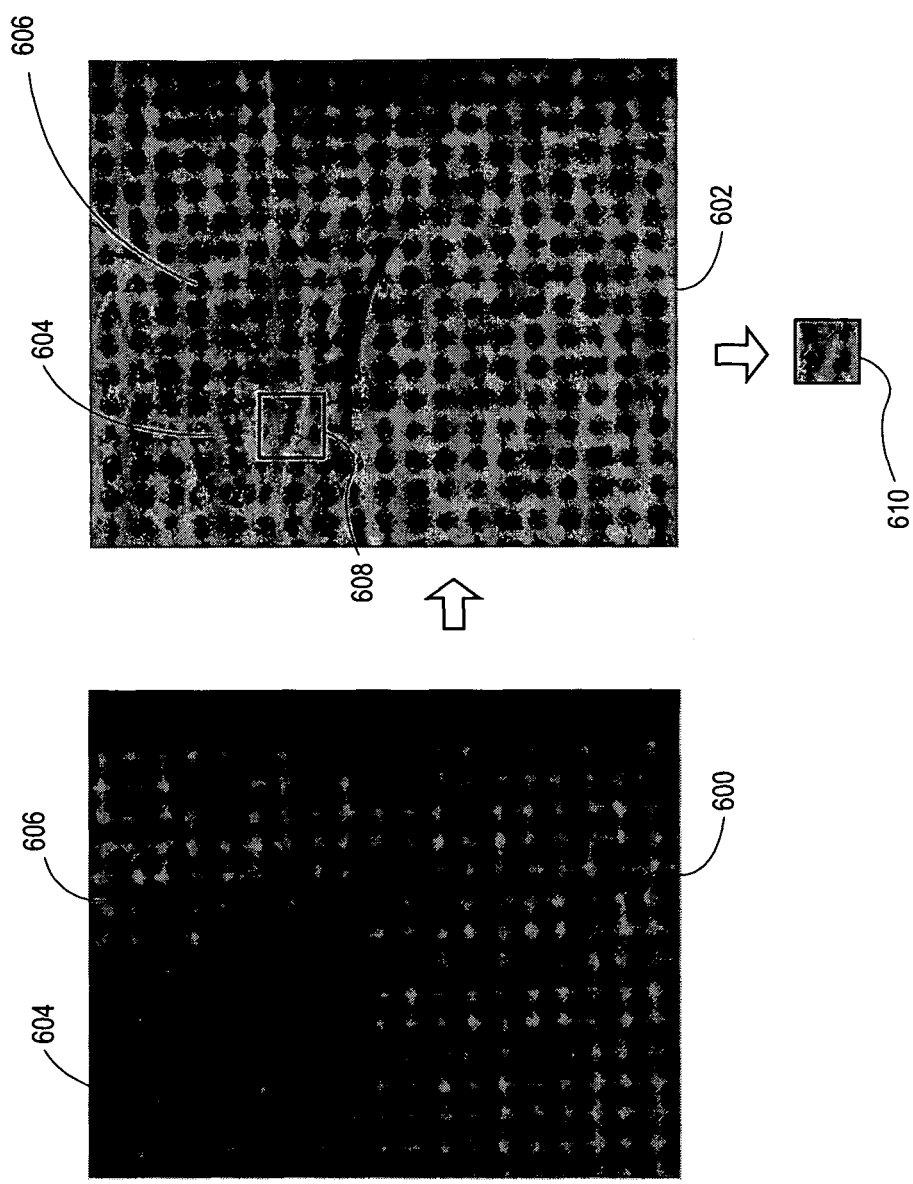
FIG. 6 shows examples of images generated at different stages of the template generation process.

FIG. 6 shows examples of images generated at different stages of the template generation process 500 described previously. An example of a reference fluoroscopic image 600 created during a phase of a respiratory cycle, and its corresponding motion enhanced fluoroscopic image 602 created using the technique described with reference to step 508 are shown. As can be seen in the figure, by subtracting the composite image of previously generated reference fluoroscopic images from the current reference fluoroscopic image, the moving object(s), i.e., the lung tissue 604, is enhanced while the contrast of the stationary object(s), i.e., the bone 606, is minimized. Furthermore, FIG. 6 shows a ROI 608 in the fluoroscopic image 602 that has been selected as a template 610. Note that the input fluoroscopic image 400 described previously with reference to FIG. 4 is similar to the reference fluoroscopic image 600 because (1) the images 400 and 600 are collected from substantially the same angle and position relative to the patient 30, and (2) the input fluoroscopic image 400 and the reference fluoroscopic image 600 are collected at substantially the same time-point of a physiological cycle.

Figure 7:
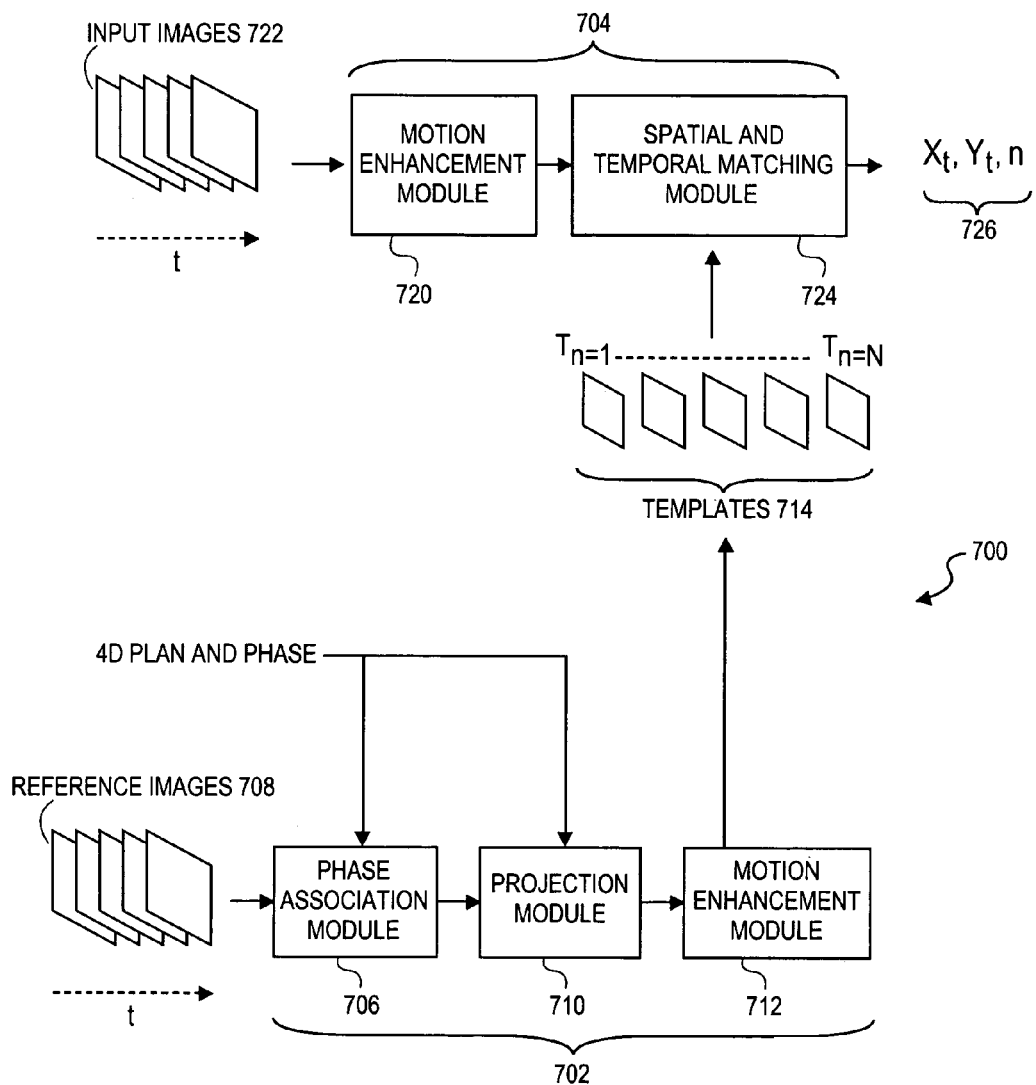
FIG. 7 is a block diagram showing a system for processing images in accordance with an embodiment of the invention.

FIG. 7 shows a system 700 for performing the above described processes. The system 700 includes a template generation module 702 and an image matching module 704, either or both of which may be implemented using the processor 14 or a computer system. The template generation module 702 includes a phase association module 706, which associates the reference images 708 with phases or time-points of a physiological cycle. The template generation module 702 also includes a projection module 710 that projects a four dimensional treatment plan (3D treatment plan over time) onto the selected reference images 708, and a motion enhancement module 712 for enhancing a feature in the selected reference images 708. In one embodiment, the motion enhancement module 712 enhance a feature in the entire image for each of the selected reference images 708. In another embodiment, the motion enhancement module 712 enhances a feature in only the projected overlay on the selected reference images 708. Also in another embodiment, the motion enhancement module 712 is optional, in which case, the system 700 does not include the motion enhancement module 712.

The image matching module 704 includes a motion enhancement module 720 for enhancing a feature in the input images 722 that are generated during a treatment or diagnostic session. The image matching module 704 also includes a spatial and temporal matching module 724 for matching the input images 722 with the generated templates 714. Particularly, for each of the input images 722, the spatial and temporal matching module 724 selects a template 714 that best matches an image in the input image 722, and generates an output 726. The output 726 includes the position $(X_n, Y_n)$ of the sub-image in the input image 722 that best matches the template $T_n$, and an index n of the best-matching template $T_n$. The index n may be used to determine the time-point or phase of a physiological cycle at which the input image 722 is generated.

The previously described method allows a user determine a position of the target region 34 during a session without the use of a radio-opaque marker, and may be implemented using existing imaging systems. The method may be used by a physician to perform a wide range of operations or procedures.

Dynamic Targeting

In one embodiment, the position of the target region 34 obtained using the previously described process may be used as an input signal to control and aim a radiation treatment beam 29 towards the target region 34. In this case, the radiation treatment beam 29 is continuously positioned to follow the target region 34 based on the positions of the target region 34 identified in the fluoroscopic images. For example, the aim point of a treatment radiation beam may be controlled by a moving collimator based on data regarding the position of the target region 34 received from the processor 14. Alternatively a treatment couch supporting a patient can be moved to control a position of the target region 34 at which the beam 29 is directed.

Physiological Gating

In another embodiment, the above-described method may be used to detect a movement of the target region 34, based on which a medical procedure may be gated. Several examples of applications towards physiological gating will now be described with reference to radiation therapy. However, it should be understood by those skilled in the art that similar techniques or methods may be used to control other types of treatments or diagnostic procedures.

In one embodiment, the radiation source 28 may be gated to be turned on or off based on the positions of the target region 34 identified in the input fluoroscopic images. In this case, the position of the image within the input fluoroscopic image that is registered with the corresponding template may be used to determine if the target region 34 has moved beyond a prescribed threshold position. If the target region 34 remains within the prescribed threshold position, the radiation beam 29 is turned on, and if the target region 34 has moved beyond the threshold position, the radiation beam 29 is then deactivated.

Figure 8:
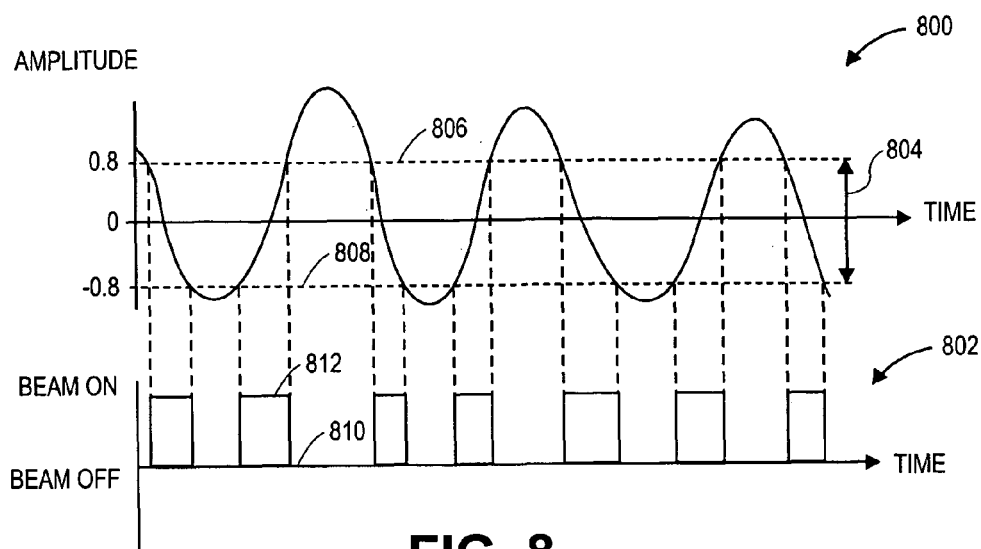
FIG. 8 shows a motion signal chart and a gating signal chart.

FIG. 8 shows an example of a motion signal chart 800 and a gating signal chart 802 that is aligned with the motion signal chart 800. The motion signal chart 800 may be created by using position data of the target region 34 obtained using the previously described process 200. A treatment interval 804 may be defined by an upper bound 806 and a lower bound 808, as shown in the motion signal chart 800. In the illustrated example, the upper bound 806 has a value of 0.8 and the lower bound 808 has a value of −0.8. As shown in the gating signal chart 802, any position of the target region 34 that falls outside the prescribed treatment interval 804 results in a "beam off" gating signal 810 that stops the application of radiation to the patient 30. Any position of the target region 34 that falls within the prescribed treatment interval 804 results in a "beam on" gating signal 812 that allows radiation to be applied to the patient 30.

In another embodiment, the radiation source 28 may be gated to be turned on or off based on the phase of a physiological cycle. In this case, the position vs. time history of the image within the input fluoroscopic image that is registered with the corresponding template may be used to determine a phase of a physiological cycle. If the target region 34 remains within a prescribed phase interval, the radiation beam 29 is turned on, and if the target region 34 has moved beyond the prescribed phase interval, the radiation beam 29 is then deactivated.

Figure 9:
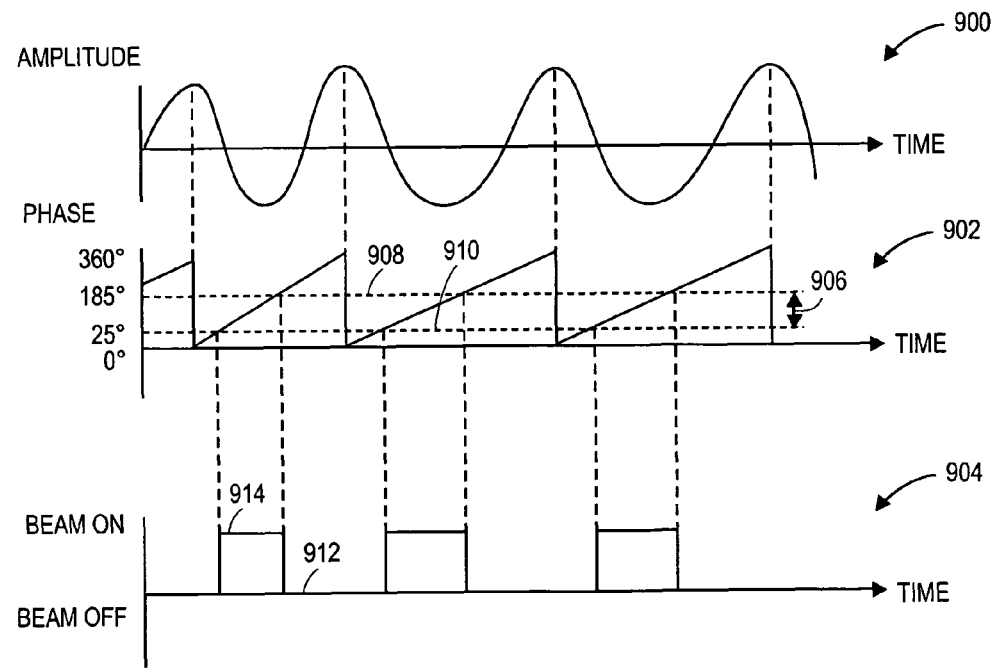
FIG. 9 shows a motion signal chart, a phase chart, and a gating signal chart.

FIG. 9 shows an example of a motion signal chart 900, a corresponding phase chart 902 for the target region 34, and a gating signal chart 904 that is aligned with the phase chart 902. The motion signal chart 900 may be created by using position data of the target region 34 obtained using the previously described method (i.e., at step 210). The phase chart 902 may be created based on a beginning and an end of a physiological cycle in the motion signal chart 900. The phase chart 902 shows the phase progression of a physiological movement of the target region 34 over time. A prescribed phase interval 906 may be defined by an upper bound 908 and a lower bound 910, which are represented as dotted lines in the phase chart 902. In the illustrated example, the upper bound 908 has a value of 185° and the lower bound 910 has a value of 25°. According to the illustrated gating signal chart 904, any position of the target region 34 corresponding to a phase that falls outside the prescribed phase interval 906 results in a "beam off" gating signal 912 that stops the application of radiation to the patient 30. Any position of the target region 34 corresponding to a phase that falls within the prescribed phase interval 906 results in a "beam on" gating signal 914 that allows radiation to be applied to the patient 30.

In yet another embodiment, the radiation treatment beam may be gated to be turned on or off by associating the templates with treatment data. In one embodiment, certain templates may be associated with a "beam on" signal, while the rest of the templates are associated with a "beam off" signal. For example, templates generated within a prescribed treatment phase interval may be associated with a "beam on" signal, while templates generated outside the prescribed treatment phase interval may be associated with a "beam off" signal. In an alternative embodiment, in addition to the "beam off" and "beam on" signals, the treatment data may also include a "beam on duration" signal. In other embodiments, the templates may also be associated with treatment data that are commonly used in radiation therapy, such as beam shape data and radiation dosage data. During a radiation treatment session, real time input fluoroscopic images are obtained and are registered with the templates in accordance with the previously described method. When an input fluoroscopic image is registered with a template that contains a "beam on" signal, the treatment radiation source 28 then directs a treatment radiation beam 29 towards the target region 34 for a duration prescribed by the corresponding "beam on duration" signal. On the other hand, when an input fluoroscopic image is registered with a template that contains a "beam off" signal, the treatment radiation source 28 then holds off the treatment beam 29 and seizes directing radiation towards the target region 34. If a template also contains a "beam shape" data, when an input fluoroscopic image is registered with such template, the processor 14 then directs a signal to a beam-shaping (e.g., a multi-leaf) collimator to change the shape of the treatment beam 29 based on the "beam shape" data. In one embodiment, to ensure that a correct treatment is being delivered to the target region 34, values may be computed to indicate a degree of correlation between the previously generated input fluoroscopic images and their corresponding registered templates. If the value indicates that there has been a high correlation in the temporal and/or spatial matching between the previously generated input fluoroscopic images and their corresponding registered templates, the registered template for the current input fluoroscopic image is likely to be correct, and treatment may be applied in accordance with the treatment data prescribed by the corresponding registered template.

In yet another embodiment, radiation may be delivered to the patient during a desired portion of a physiological cycle. In radiation therapy, it may be desirable to apply the radiation beam 29 towards the target region 34 during a portion, such as a quiescent period, of a physiological cycle. For example, quiescent periods occur during the respiratory cycle at the ends of expiration and inspiration. In this case, the determined position of the target region 34 can be used to detect quiescent periods of physiological cycles. During the quiescent periods, the motion of the target region 34 slows down or may even cease for a fraction of a moment, thereby allowing a radiation treatment to be directed to the target region 34.

It should be noted that in the above described embodiments, the activation of a radiation beam may be gated in substantially real-time, or alternatively, in a predictive fashion. For example, based on a detected position of a target region and a degree of match between previous input fluoroscopic images and the templates, the processor 14 can predictively activate a radiation source (an example of predictive gating) so as to compensate for delay of activation time inherent in some x-ray systems. Predictive gating has been described in U.S. patent application Ser. No. 09/893,122 referenced herein.

Figure 10:
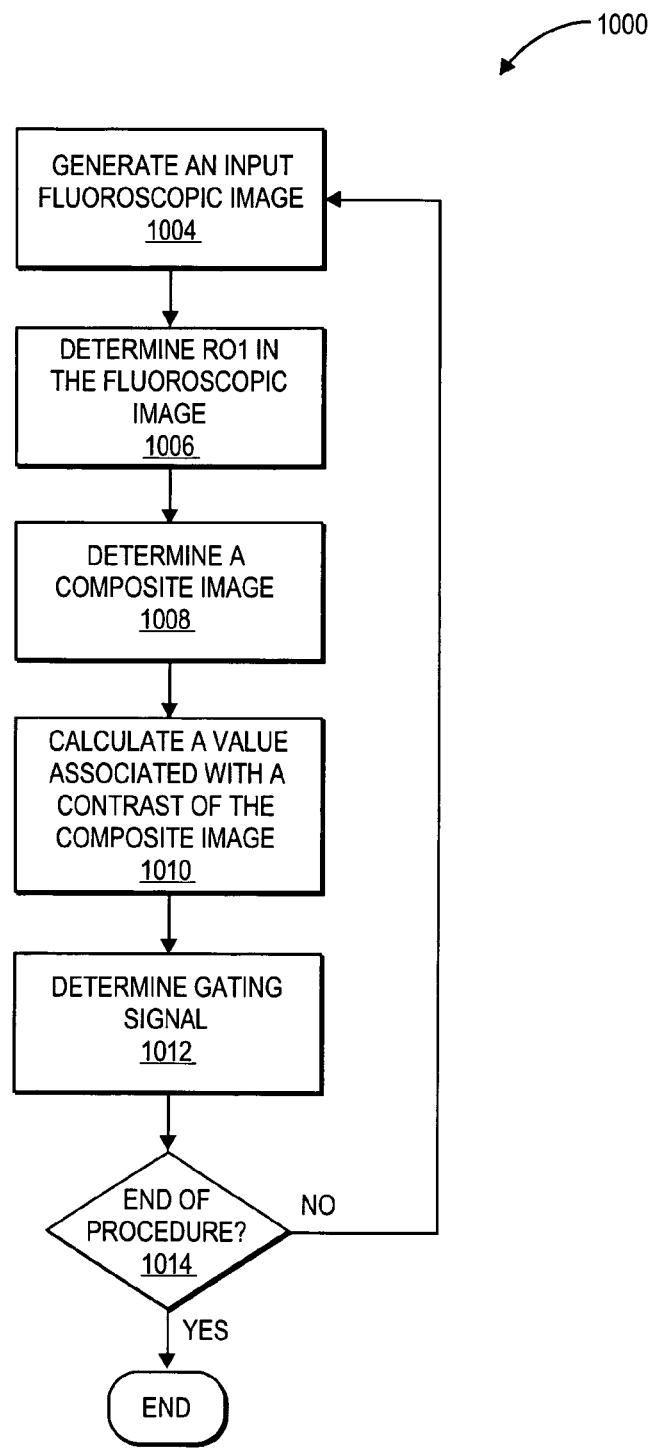
FIG. 10 is a flowchart showing a process for gating a medical procedure in accordance with an embodiment of the invention.

FIG. 10 shows a method 1000 for gating a medical treatment based on a degree of detected motion of the target region 34 in accordance with an embodiment of the present invention.

To gate a medical treatment on the target region 34 of the patient 30 undergoing a fluoroscopic imaging, a real-time input fluoroscopic image is generated using the fluoroscopic system 10 of FIG. 1 (Step 1004).

Next, a ROI in the input fluoroscopic image is determined (Step 1006). In one embodiment, the ROI includes at least a portion of the target region 34, which can be a tissue targeted for treatment, or alternatively, any other tissue captured in the input fluoroscopic image. The ROI can be determined by a physician during a treatment or planning session. For example, the ROI may be defined by a frame circumscribing a portion of the input fluoroscopic image.

Next, a composite image CI is created by subtracting the image in the ROI in the previous input fluoroscopic image from the image in the ROI in the current input fluoroscopic image (Step 1008). For example, for the third input fluoroscopic image $IFI_3$ generated in a sequence, a corresponding composite image $CI_3$ is created by subtracting the image in the ROI in the previous input fluoroscopic image (i.e., the second fluoroscopic image $IFI_2$) from the third input fluoroscopic image $IFI_3$ (i.e., $CI_n = IFI_n - IFI_{n-1}$). It should be understood that this step needs not be performed for the first input fluoroscopic image in the sequence since there is no previous input fluoroscopic image before the first input fluoroscopic image.

A value associated with a contrast of the composite image is next calculated over the ROI (1010). In one embodiment, the variance of the pixels in the composite image, which is associated with a contrast of the composite image CI, may be calculated over the ROI, and may be used as a measure of the extent of motion undergone by the tissue within the ROI (e.g., the target region 34). In other embodiments, different measures of the contrast in the composite image may be used.

A beam gating signal is determined based on the calculated value (1012). Since an image of an object in the ROI having low contrast indicates that the object has not moved significantly over time, and vice versa, a radiation beam may be disabled when the calculated value (associated with the contrast of the composite image in the ROI) exceeds a certain threshold, and be enabled when the value is below the threshold. In one embodiment, if the calculated value m>T. A, then a radiation beam is disabled, and vice versa, where T is a prescribed threshold value, and A is a normalization factor for compensating for changes or daily variations in the operation of the fluoroscopic imaging system 10. One possible value for A is A=|max m(t)−min m(t)| where max m(t) and min m(t) are derived from observing m over a recent physiological cycle, such as a respiratory cycle or a cardiac cycle.

The next real-time input fluoroscopic image is generated and the previously described process is repeated until a sufficient radiation has been delivered to the target region 34 (Step 1014).

Target Object Position Monitoring

Besides dynamically targeting a moving object and gating a medical procedure, methods similar to that described previously may also be used to monitor or determine the position of a target object during a session. The target object may be a patient or an internal organ.

In one embodiment, a position of the object 30 may be determined using a method that is similar to that discussed previously with reference to FIG. 2. In this case, instead of generating a sequence of templates, one template is generated using the process 500 discussed previously. In this case, a portion of the reference fluoroscopic image containing the target object (i.e., object that is not expected to move beyond a certain prescribed threshold during a session) is selected as the template. During a treatment or diagnostic session, input fluoroscopic images of the target object 30 are analyzed and compared with the template to determine the position of the object in the input fluoroscopic images. For example, the processor 14 may perform image analysis to determine a portion in each of the input fluoroscopic images that best matches with the template. The position of the matched portion in each of the input fluoroscopic images represents the position of the object. By observing the determined positions of the object in the input fluoroscopic images, one can determine how much the target object 30 has moved during a session. With respect to radiation therapy, if it is determined that the object 30 has moved beyond a certain prescribed threshold, the radiation beam 29 may be deactivated.

Figure 11:
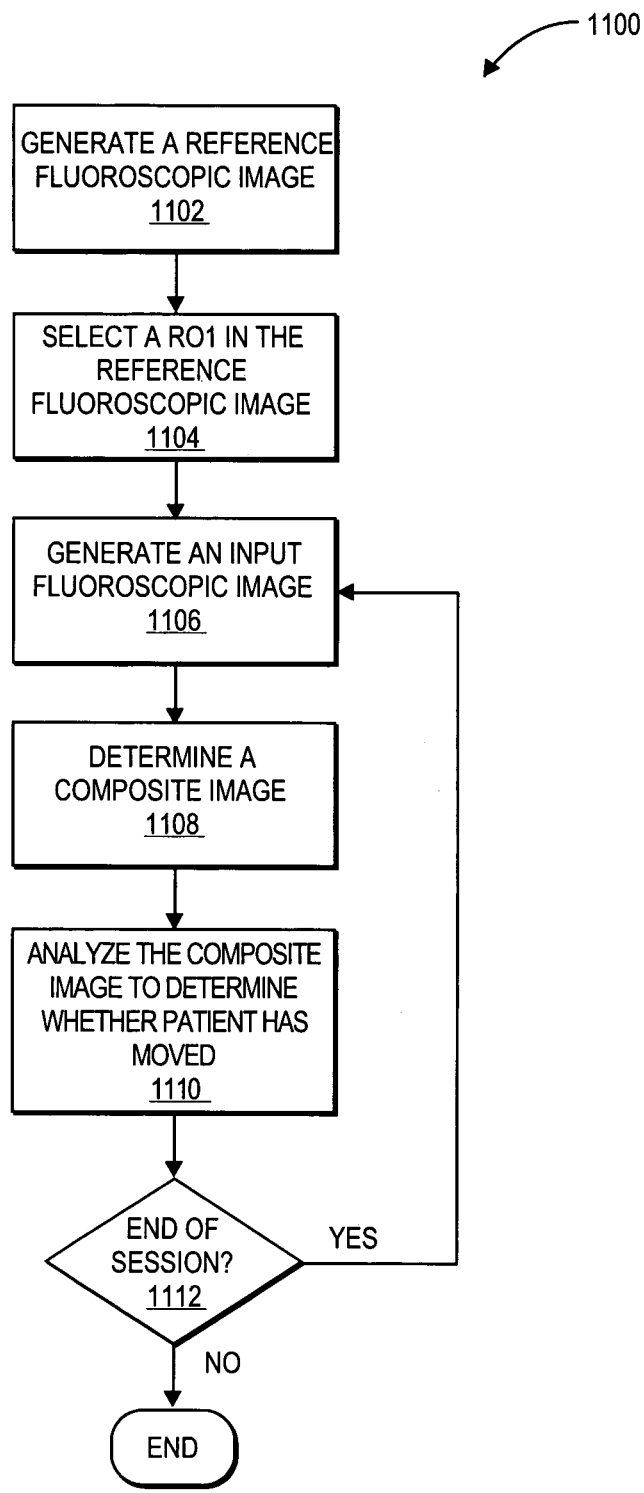
FIG. 11 is a flowchart showing a process for monitoring a patient's position in accordance with an embodiment of the invention.

In certain situations, it may be desirable to determine that there is target object movement, and it may not be necessary to determine how much an object has moved. FIG. 11 shows a method 1100 for target object position monitoring (i.e., determining whether there is target object movement) in accordance with an embodiment of the present invention. First, the radiation source 22 of the fluoroscopic system 10 and the image detector is positioned and aimed towards the target object 30, and a reference fluoroscopic image RFI is generated using the fluoroscopic system 10 (Step 1102).

Next, a portion of the reference fluoroscopic image is selected as a ROI (Step 1104). Particularly, the portion of the reference fluoroscopic image should contain an image of a target object, that is expected to be held relatively stationary during a treatment or diagnostic session. The position of the ROI in the reference fluoroscopic image may be stored in a computer-readable medium for later use.

To perform target object position monitoring during a treatment or diagnostic session, a real-time input fluoroscopic image $IFI_n$ is generated using the fluoroscopic system 10 (Step 1106). In the illustrated embodiment, the reference fluoroscopic image and the input fluoroscopic image are generated in the same session with the patient 30 staying in substantially the same position. Alternatively, the reference fluoroscopic image and the input fluoroscopic image may be generated in different sessions. In this case, the x-ray source 22 and image detector are set up such that its position and orientation relative to the patient 30 are substantially the same as those in which the reference fluoroscopic image was generated.

In Step 1108, the current input fluoroscopic image $IFI_n$ is subtracted from the reference fluoroscopic image RFI over the ROI to obtain a composite image $CI_n$ (i.e., $CI_n=IFI_n-RFI$). In other words, a portion of the input fluoroscopic image $IFI_n$ having the same position as the ROI in the reference fluoroscopic image RFI is selected and subtracted from the image in the ROI to obtain the composite image $CI_n$.

The composite image $CI_n$ is then analyzed to determine whether there has been target object movement (1110). If there has been target object movement, the pixels in the composite image $CI_n$ should have an increase in contrast. The target object 30 may be considered to have moved if the contrast increase is above a certain prescribed threshold. With respect to radiation therapy, the radiation beam 29 may be deactivated when the contrast increase is above a prescribed threshold.

The next real-time input fluoroscopic image is then generated and the previously described process is repeated until the end of the session is reached (Step 1112).

The above-described target object position monitoring and determination may be performed in conjunction with the dynamic targeting or gating of a medical procedure described previously. Alternatively, other techniques for monitoring or determining a target object position, such as those described in U.S. patent application Ser. No. 09/893,122, may also be used. The entire disclosure of the U.S. patent application Ser. No. 09/893,122 is expressly incorporated by reference herein.

Computer System Architecture

Figure 12:
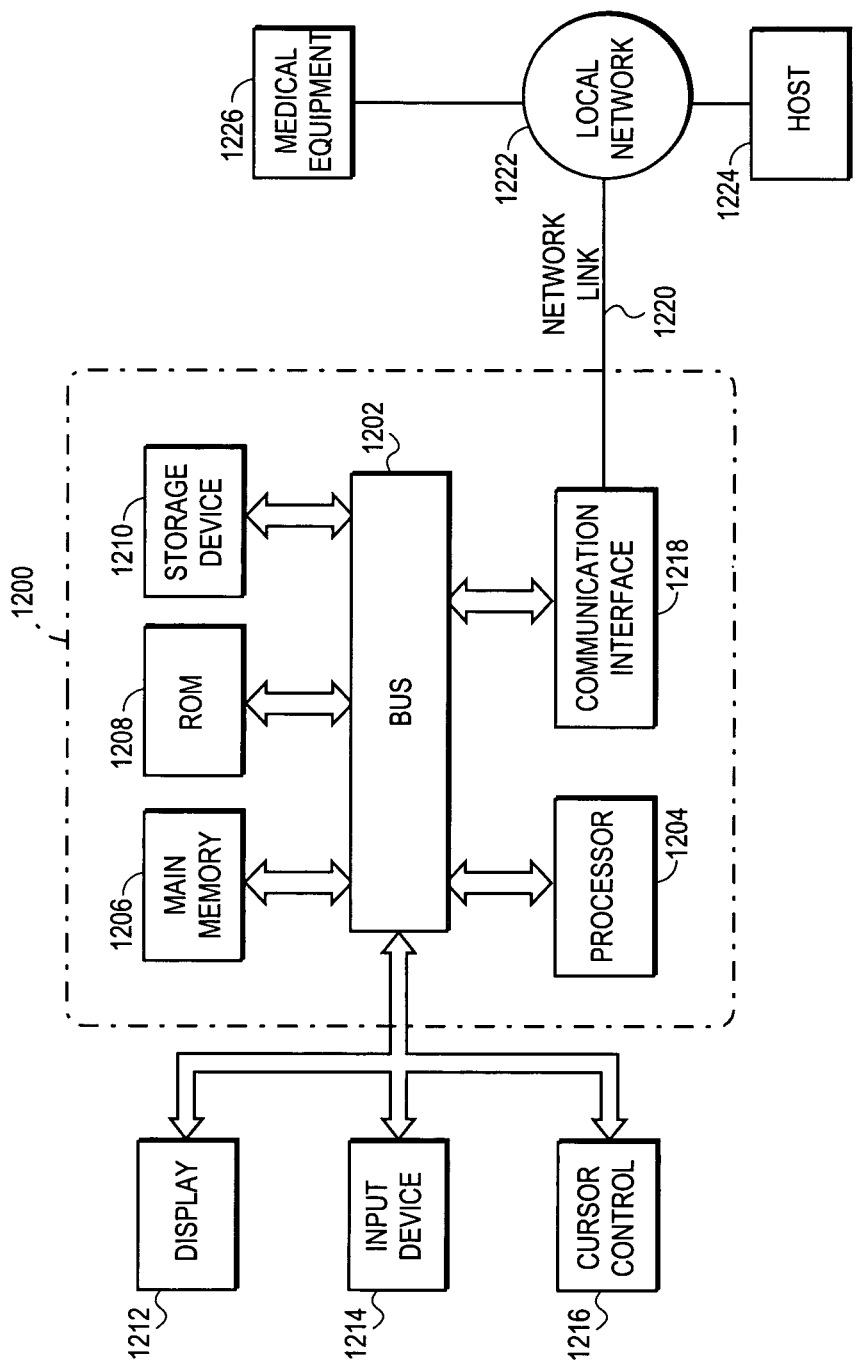
FIG. 12 is a diagram of a computer hardware system with which embodiments of the present invention can be implemented.

FIG. 12 is a block diagram that illustrates an embodiment of a computer system 1200 upon which an embodiment of the invention may be implemented. Computer system 1200 includes a bus 1202 or other communication mechanism for communicating information, and a processor 1204 coupled with the bus 1202 for processing information. The processor 1204 may be an example of the processor 14 of FIG. 1. The computer system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The computer system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The computer system 1200 may be coupled via the bus 1202 to a display 1212, such as a cathode ray tube (CRT), for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The invention is related to the use of computer system 1200 for processing images. According to one embodiment of the invention, such use is provided by computer system 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media includes, for example, optical or magnetic disks, such as the storage device 1210. Volatile media includes dynamic memory, such as the main memory 1206. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the computer system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The computer system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to medical equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the computer system 1200, are exemplary forms of carrier waves transporting the information. The computer system 1200 can send messages and receive data, including program code, through the network(s), the network link 1220, and the communication interface 1218.

Although the embodiments of the systems and methods have been described with reference to fluoroscopic imaging, it should be understood that the systems and methods may also be implemented using other types of imaging. Depending on the type of imaging used, the previously described methods may be modified, and are intended to be within the scope of the present invention. For example, if the type of imaging technique used is such that it can generate images of a target region with sufficient contrast or desired features, then the step (i.e., step 206 and 508) of enhancing a moving object in an image may not be necessary. Particularly, in other embodiments, if the contrasts or features of an image in the templates and the input images are such that they allow registration between the templates and the input images, then the methods 200 and 500 may not include step 206 and 508, respectively.

Although the methods have been described with reference to radiation treatment, it should be understood that the same or similar methods may also be used to perform other types of medical procedures. For example, the gating methods described with reference to FIGS. 8-10 may be used in various diagnostic imaging procedures as well as image-guided surgery in which movement of surgical instruments are controlled by the position of the target object. In addition, besides real-time and predictive gating described previously, the above-described methods may also have applications in retrospective gating. In this case, the input fluoroscopic images or the processed input fluoroscopic images can be time-stamped and stored for future processing. For example, in three-dimensional imaging applications such as computed tomography, PET, and MRI, physiological data (e.g., position of target region or patient) obtained from the processed input fluoroscopic images can be used to retrospectively "gate" a reconstruction process. For this purpose, the raw data associated with the imaging application is synchronized to a common time base with the physiological motion data. Segments of the raw data that correspond to movement cycle intervals of interest are used to reconstruct the volumetric image thus minimizing the distortion and size changes caused by patient motion.

Furthermore, the method 200 is not limited to determining a position of a portion of a patient or animal body. The method 200 may also be used to determine a position of a non-animal body or other objects in a medical or non-medical environment.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. For example, the operations performed by the processor 14 can be performed by any combination of hardware and software within the scope of the invention, and should not be limited to particular embodiments comprising a particular definition of "processor". The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method of performing physiological gating in a medical procedure, wherein the method is at least partially performed using a hardware processor, comprising:
   acquiring a sequence of images, wherein each of the images in the sequence is generated using a same imaging device, the sequence of images comprises at least a first image and a second image of a target region;
   determining a first composite image based at least in part on the first and second images, wherein the determining comprises performing an image subtraction using the first and second images from the sequence;
   gating a medical procedure based at least in part on the first composite image, wherein the act of gating the medical procedure is performed in real time using the processor; and
   determining a first value associated with a contrast of the first composite image;

wherein the gating the medical procedure is performed based at least on the first value; and wherein the gating comprises de-activating a radiation beam when the first value is above a prescribed threshold value.

2. The method of claim 1, wherein the determining the first composite image comprises subtracting the first image from the second image.

3. The method of claim 1, wherein the medical procedure comprises a radiation treatment procedure.

4. The method of claim 1, further comprising:
acquiring a third image of the target region;
determining a second composite image based on the second and third images; and
gating the medical procedure based on the second composite image.

5. The method of claim 1, wherein the sequence of images are fluoroscopic images.

6. The method of claim 1, wherein the sequence of images are real-time images created during a session.

7. The method of claim 1, wherein the act of acquiring the sequence of images is performed during a treatment session.

8. A system for performing physiological gating in a medical procedure, comprising:
means for acquiring a sequence of images, wherein each of the images in the sequence is generated using a same imaging device, the sequence of images comprises at least a first image and a second image of a target region;
means for determining a first composite image based at least in part on the first image and the second image, wherein the means for determining is configured to perform an image subtraction using the first and second images from the sequence;
means for gating a medical procedure in real time based at least in part on the first composite image; and
means for determining a first value associated with a contrast of the first composite image;
wherein the means for gating the medical procedure performs the gating based at least on the first value; and
wherein the means for gating comprises means for deactivating a radiation beam when the first value is above a prescribed threshold value.

9. The system of claim 8, wherein the medical procedure comprises a radiation treatment procedure.

10. The system of claim 8, wherein the means for acquiring the sequence of images is configured to acquire the sequence of images during a treatment session.

11. A computer readable non-transitory medium having a set of stored instructions, the execution of which by a processor causes at least a portion of a process to be performed, the process comprising:
acquiring a sequence of images, wherein each of the images in the sequence is generated using a same imaging device, the sequence of images comprises at least a first image and a second image of a target region;
determining a first composite image based at least in part on the first and second images, wherein the determining comprises performing an image subtraction using the first and second images from the sequence;
gating a medical procedure based at least in part on the first composite image, wherein the act of gating the medical procedure is performed in real time using the processor; and
determining a first value associated with a contrast of the first composite image;
wherein the gating the medical procedure is performed based at least on the first value; and
wherein the gating comprises de-activating a radiation beam when the first value is above a prescribed threshold value.

12. The computer readable medium of claim 11, wherein the determining the first composite image comprises subtracting the first image from the second image.

13. The computer readable medium of claim 11, wherein the medical procedure comprises a radiation treatment procedure.

14. The computer readable medium of claim 11, wherein the process further comprising:
acquiring a third image of the target region;
determining a second composite image based on the second and third images; and
gating the medical procedure based on the second composite image.

15. The computer readable medium of claim 11, wherein the sequence of images are fluoroscopic images.

16. The computer readable medium of claim 11, wherein the sequence of images are real-time images created during a session.

17. The computer readable medium of claim 11, wherein the act of acquiring the sequence of images is performed during a treatment session.

18. A method of performing a medical procedure, wherein the method is at least partially performed using a hardware processor, comprising:
providing a plurality of templates for treating a patient, each of the templates having an image and treatment data, wherein the treatment data comprises one or more parameters for controlling an operation of a radiation machine, each of the plurality of templates corresponds to a phase of a physiological cycle, and the treatment data in each of the templates is pre-determined before a treatment session and forms a part of the corresponding template together with the corresponding image;
acquiring an input image that is generated using an imaging device;
registering the input image with one of the templates, wherein the act of registering is performed using the processor; and
performing a medical procedure based at least in part on the treatment data of the one of the templates that is registered with the input image.

19. The method of claim 18, wherein the registering comprises selecting a template from the plurality of templates that best matches an image in the input image.

20. The method of claim 18, wherein the one or more parameters comprise one or a combination of beam-on signal, beam-off signal, beam-on duration, beam shape data, and dosage data.

21. The method of claim 18, further comprising enhancing a moving object in the input image.

22. The method of claim 21, wherein the enhancing comprises determining a composite image of previously acquired input images.

23. The method of claim 22, wherein the determining a composite image comprises performing an image averaging on the previously acquired input images.

24. The method of claim 22, wherein the enhancing further comprises subtracting the composite image from the input image.

25. The method of claim 18, wherein the medical procedure comprises directing a radiation beam to an object.

26. The method of claim 25, wherein the performing the medical procedure comprises adjusting a delivery of the radiation beam based on the treatment data.

27. A system for performing a medical procedure, comprising:
 means for providing a plurality of templates for treating a patient, each of the templates having an image and treatment data, wherein the treatment data comprises one or more parameters for controlling an operation of a radiation machine, each of the plurality of templates corresponds to a phase of a physiological cycle, and the treatment data in each of the templates is pre-determined before a treatment session and forms a part of the corresponding template together with the corresponding image;
 means for acquiring an input image;
 means for registering the input image with one of the templates; and
 means for performing a medical procedure based at least in part on the treatment data of the one of the templates that is registered with the input image.

28. The system of claim 27, wherein the means for registering comprises means for selecting a template from the plurality of templates that best matches an image in the input image.

29. The system of claim 27, further comprising means for enhancing a moving object in the input image.

30. The system of claim 27, wherein the one or more parameters comprise one or a combination of beam-on signal, beam-off signal, beam-on duration, beam shape data, and dosage data.

31. The system of claim 27, wherein the means for performing a medical procedure comprises means for directing a radiation beam to an object.

32. The system of claim 31, wherein the means for directing a radiation beam comprises means for adjusting a delivery of the radiation beam based on the treatment data.

33. A computer readable non-transitory medium having a set of stored instructions, the execution of which by a processor causes at least a portion of a process to be performed, the process comprising:
 providing a plurality of templates for treating a patient, each of the templates having an image and treatment data, wherein the treatment data comprises one or more parameters for controlling an operation of a radiation machine, each of the plurality of templates corresponds to a phase of a physiological cycle, and the treatment data in each of the templates is pre-determined before a treatment session and forms a part of the corresponding template together with the corresponding image;
 acquiring an input image that is generated using an imaging device;
 registering the input image with one of the templates, wherein the act of registering is performed using the processor; and
 performing a medical procedure based at least in part on the treatment data of the one of the templates that is registered with the input image.

34. The computer readable medium of claim 33, wherein the registering comprises selecting a template from the plurality of templates that best matches an image in the input image.

35. The computer readable medium of claim 33, wherein the process further comprising enhancing a moving object in the input image.

36. The computer readable medium of claim 35, wherein the enhancing comprises determining a composite image of previously acquired input images.

37. The computer readable medium of claim 36, wherein the determining a composite image comprises performing an image averaging on the previously acquired input images.

38. The computer readable medium of claim 36, wherein the enhancing further comprises subtracting the composite image from the input image.

39. The computer readable medium of claim 33, wherein one or more parameters comprise one or a combination of beam-on signal, beam-off signal, beam-on duration, beam shape data, and dosage data.

40. The computer readable medium of claim 33, wherein the medical procedure comprises directing a radiation beam to an object.

41. The computer readable medium of claim 40, wherein the performing the medical procedure comprises adjusting a delivery of the radiation beam based on the treatment data.

42. A method of performing physiological gating in a medical procedure, wherein the method is at least partially performed using a hardware processor, comprising:
 providing a template;
 acquiring an input image of a target region, wherein the input image is generated using an imaging device;
 enhancing a moving object in the input image based on a movement of the object, wherein the object comprises a part of the target region;
 registering the input image with the template, wherein the registering comprises selecting the template from a plurality of templates that best matches an image in the input image;
 determining a position of the target region based at least in part on the registering; and
 gating a medical procedure using the processor based at least in part on the determined position of the target region.

43. The method of claim 42, wherein the act of enhancing the moving object in the input image is performed only when the object moves.

44. The method of claim 42, wherein the enhancing comprises subtracting an average of previously acquired input images from the input image.

45. The method of claim 42, wherein the determining the position of the target region comprises determining a position of the image in the input image that best matches with the template.

46. The method of claim 42, wherein the medical procedure comprises a radiation treatment, and the gating comprises activating or deactivating a radiation beam based on the determined position of the target region.

47. A system for performing physiological gating in a medical procedure, comprising:
 means for providing a template;
 means for acquiring an input image of a target region;
 means for enhancing a moving object in the input image based on a movement of the object, wherein the object comprises a part of the target region;
 means for registering the input image with the template, wherein the means for registering comprises means for selecting the template from a plurality of templates that best matches an image in the input image;
 means for determining a position of the target region based at least in part on the registering; and
 means for gating a medical procedure based at least in part on the determined position of the target region.

48. The system of claim 47, wherein the medical procedure comprises a radiation treatment, and the means for gating comprises means for activating or deactivating a radiation beam based on the determined position of the target region.

49. A computer readable non-transitory medium having a set of stored instructions, the execution of which by a processor causes at least a portion of a process to be performed, the process comprising:

providing a template;

acquiring an input image of a target region, wherein the input image is generated using an imaging device;

enhancing a moving object in the input image based on a movement of the object, wherein the object comprises a part of the target region;

registering the input image with the template, wherein the registering comprises selecting the template from a plurality of templates that best matches an image in the input image;

determining a position of the target region based at least in part on the registering; and gating a medical procedure using the processor based at least in part on the determined position of the target region.

50. The computer readable medium of claim 49, wherein the act of enhancing the moving object in the input image is performed only when the object moves.

51. The computer readable medium of claim 49, wherein the enhancing comprises subtracting an average of previously acquired input images from the input image.

52. The computer readable medium of claim 49, wherein the determining the position of the target region comprises determining a position of the image in the input image that best matches with the template.

53. The computer readable medium of claim 49, wherein the medical procedure comprises a radiation treatment, and the gating comprises activating or deactivating a radiation beam based on the determined position of the target region.

* * * * *

UNITED STATES PATENT AND TRADEMARK OFFICE
CERTIFICATE OF CORRECTION

| | | |
|---|---|---|
| PATENT NO. | : 8,571,639 B2 | Page 1 of 1 |
| APPLICATION NO. | : 10/655920 | |
| DATED | : October 29, 2013 | |
| INVENTOR(S) | : Mostafavi | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 761 days.

Signed and Sealed this
Seventh Day of April, 2015

Michelle K. Lee
*Director of the United States Patent and Trademark Office*